(12) United States Patent
Berzofsky et al.

(10) Patent No.: US 6,685,944 B1
(45) Date of Patent: Feb. 3, 2004

(54) MODIFIED HCV PEPTIDE VACCINES

(75) Inventors: Jay A. Berzofsky, Bethesda, MD (US); C. David Pendleton, Bethesda, MD (US); Stephen M. Feinstone, Washington, DC (US); Marian E. Major, Alexandria, VA (US); Pablo Sarobe, Pamplona (ES)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/763,260

(22) PCT Filed: Aug. 17, 1999

(86) PCT No.: PCT/US99/18674

§ 371 (c)(1),
(2), (4) Date: Oct. 19, 2001

(87) PCT Pub. No.: WO00/11186

PCT Pub. Date: Mar. 2, 2000

Related U.S. Application Data

(60) Provisional application No. 60/097,446, filed on Aug. 21, 1998.

(51) Int. Cl.⁷ ............................................. A61K 39/29
(52) U.S. Cl. ........................ 424/189.1; 435/5; 435/7.24; 435/320.1; 424/228.1; 514/15; 530/327; 530/350; 536/23.72
(58) Field of Search .......................... 514/15; 530/328, 530/350; 536/23.72; 435/5, 7.24, 320.1; 424/189.1, 228.1

(56) References Cited

U.S. PATENT DOCUMENTS 5,709,995 A * 1/1998 Chisari et al. ................. 435/5

FOREIGN PATENT DOCUMENTS

| WO | WO 95/12677 | 5/1995 |
| WO | WO 95/27733 | 10/1995 |
| WO | WO 97/41440 | 11/1997 |

OTHER PUBLICATIONS

Parker et al., Sequence motifs important for peptide binding to the human MHC class I molecule HLA–A2. The Journal of Immunology 149: 3580–3587, 1992.*

Kalams et al., T Cell Receptor Usage and Fine Specificity of Human Immunodeficiency Virus 1–specific Cytotoxic T Lymphocyte Clones. Journal of Experimental Medicine 183:1669–1679, 1996.*

Hudrisier et al., Relative Implication of Peptide Residues in Binding to Major Histocompatibility Complex Class I H–2Db: Application to the Design of High–Affinity, Allele–Specific Peptides. Molecular Immunology 32:895–907, 1995.*

Sarobe et al. "Enhanced in vitro potency and in vivo immunogenicity of a CTL epitope from hepatitias C virus core protein following amino acid replacement at secondary HLA–A2.1 binding positions" *J. Clin. Invest.*, 102(6):1239–1428 (Sep. 1998).

Ahlers et al. "Enhanced immunogenicity of HIV–1 vaccine construct by modification of the native peptide sequence" *Proc. Natl. Acad. Sci. USA*, 94:10856–10861 (Sep. 1997).

Shirai et al. "CTL responses of HLA–A2.1–transgenic mice specific for hepatitis C viral peptides predict epitopes for CTL of humans carrying HLA–A2.1" *J. Immund.*, 154(6):2733–2742 (Mar. 1995).

\* cited by examiner

*Primary Examiner*—Donna C. Wortman
(74) *Attorney, Agent, or Firm*—Needle & Rosenberg, P.C.

(57) ABSTRACT

The present invention provides 1) an isolated peptide having the amino acid sequence DLMGYIPAV, (SEQ ID NO: 1); 2) an isolated HCV core polypeptide comprising an L→A substitution at amino acid position 139; 3) an isolated HCV core polypeptide having the amino acid sequence of SEQ ID NO: 2; and 4) a fragment of an HCV core polypeptide having fewer amino acids than the entire HCV core polypeptide and comprising the amino acid sequence SEQ ID NO: 1. Also provided are nucleic acids which encode the peptides and polypeptides of this invention, vectors comprising the nucleic acids of this invention and cells comprising the vectors and nucleic acids of this invention. The present invention further provides methods of producing an immune response in a subject and/or treating or preventing HCV infection in a subject, comprising administering to the subject, or to a cell of the subject, any of the compositions of this invention.

16 Claims, 9 Drawing Sheets

SEQUENCE LISTING

<160> NUMBER OF SEQ ID NOS: 8

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 1

Asp Leu Met Gly Tyr Ile Pro Ala Val
1               5

<210> SEQ ID NO 2
<211> LENGTH: 191
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 2

Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Ala Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 3

Asp Leu Met Gly Tyr Ile Pro Leu Val
1               5

```
<210> SEQ ID NO 4
<211> LENGTH: 191
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 4

Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65              70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
                180                 185                 190

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 5
tcatggggta cataccggcg gtc                                              23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 6
tccaagaggg gcgccgaccg ccg                                              23

<210> SEQ ID NO 7
<211> LENGTH: 21
<212> TYPE: DNA
<213> ORGANISM: Artificial Sequence
<220> FEATURE:
```

-continued

```
<223> OTHER INFORMATION: Description of Artificial Sequence:/Note =
      synthetic construct

<400> SEQUENCE: 7
aagactgcta gccgagtagt g                                              21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 8
cacaatactc gagttagggc                                                20
```

MODIFIED HCV PEPTIDE VACCINES

This application claims benefit of Provisional application Ser. No. 60/097,446 filed Aug. 21, 1998.

BACKGROUND OF THE INVENTION

1. Field of the Invention

The present invention relates to the field of viral vaccines. In particular, the present invention relates to modification of immunogenic epitopes of the hepatitis C virus (HCV) core protein to elicit an enhanced immune response against HCV.

2. Background Art

Hepatitis C virus (HCV) is a single stranded RNA virus responsible for the majority of non-A non-B hepatitis (1). Infection by HCV frequently evolves to chronicity and in many cases leads to liver cirrhosis and hepatocellular carcinoma (2). The cellular immune response is thought to be responsible for viral clearance in many viral infections (3–7) and in the case of HCV, a cytotoxic T lymphocyte (CTL) response is present in acutely and chronically infected patients (8–14), but its role in viral clearance has not been elucidated. CTL responses have been detected in peripheral blood mononuclear cells (PBMC) and in intrahepatic lymphocytic infiltrate in patients with chronic hepatitis (15) and in the liver of infected chimpanzees (16), indicating that in these cases the virus is able to persist despite this immune response (17). The reasons for the inadequacy of this immune response in chronically infected patients are not known (18).

$CD8^+$ CTL recognize antigens as peptides presented by class I molecules of the major histocompatibility complex (MHC) on the cell surface. These peptides are usually 8–10 amino acids long and are generated after processing of intracellular antigens (3,19–21). Analysis of peptides presented by MHC class I molecules has led to the definition of several sequence patterns or motifs (22–24) for peptides that bind to each particular MHC allele or group of alleles (supermotif) (25). These motifs are based on the presence in precise positions in the peptide sequence of several amino acids (agretopic residues) called anchor residues (22,26), responsible for interactions between peptide and MHC molecule, as well as other secondary positions that may help in stabilizing these interactions (27–29). The use of these motifs to identify peptides able to bind to MHC molecules, together with the development of MHC-peptide binding assays, has led to the characterization of many CTL epitopes in the HCV polypeptide presented by different MHC molecules (9,10,12,30). Among the best studied motifs is that of HLA-A2.1, which is prevalent in a high percentage of the population (31). Several reports describe the binding motif for this allele, pointing out the importance of anchor as well as secondary residues. Also, MHC binding has been correlated with immunogenicity in different mouse and human systems (30,32–37).

Despite the presence of the typical anchor residues, the binding capability of a peptide epitope may vary, depending on the other secondary residues. Thus, the presence of certain amino acids in secondary positions may enhance or impair a peptide's binding ability (28,38,39). Other amino acids (epitopic residues) are responsible for recognition by the T cell receptor (TCR). Thus, T cell response is triggered by interactions in the trimolecular complex: MHC-antigenic peptide-TCR, together with other co-stimulatory molecules (40,41). These interactions occur between the antigenic peptide and pockets in the structure of both MHC and TCR molecules and changes in the amino acid sequence of the peptide may affect any of these interfaces.

Because of the inadequacy of the immune response in HCV-infected individuals, there exists a great need to enhance the immune response to HCV immunogenic epitopes without impairing MHC binding affinity or T cell recognition. The present invention overcomes the previous limitations and shortcomings in the art by providing immunogenic peptides of HCV core protein which elicit an enhanced immune response, methods for making these peptides and methods for using these peptides for a variety of therapeutic, diagnostic and prognostic applications.

Figure 1:
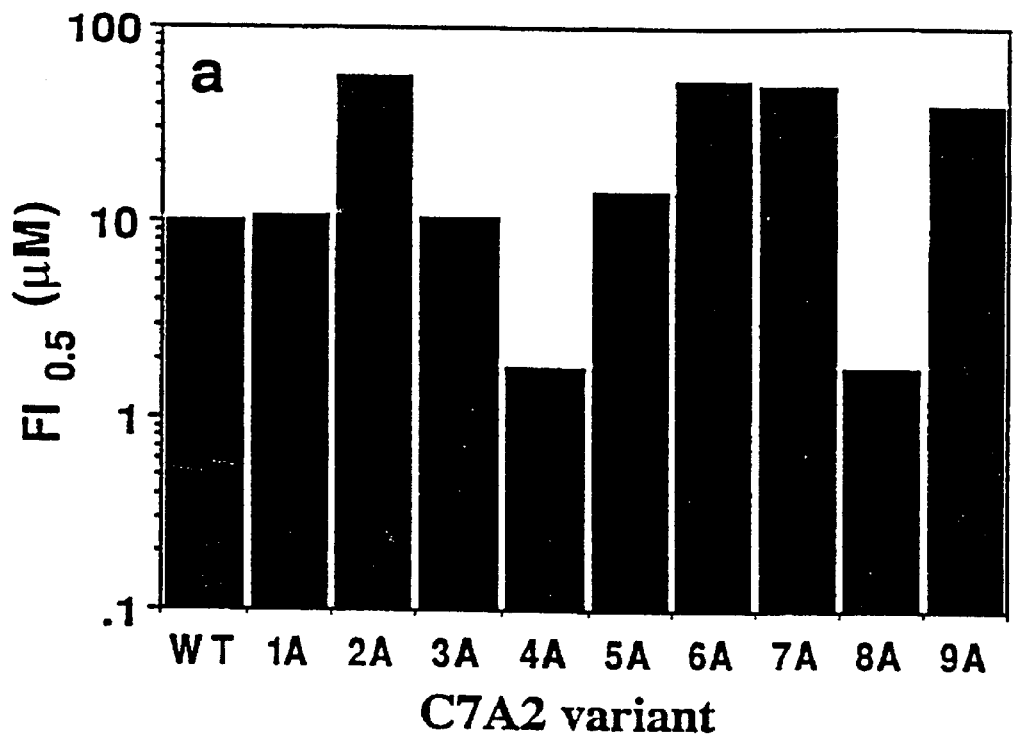
FIGS. 1A and 1B. Binding of C7A2 Alanine (A) and non-Alanine (B)-substituted peptides to TAP-deficient HLA-A2.1. T2 cells were incubated overnight in a 96 well plate in CTM with 10 µg/ml human β2-microglobulin and different peptide concentrations. The next day, cells were washed and HLA-A2.1 expression was assessed by flow cytometry using the anti HLA-A2 BB7.2 monoclonal antibody and FITC labeled goat anti mouse Ig. Results are expressed as fluorescence index (FI), calculated according to the formula: (mean fluorescence with peptide-mean fluorescence without peptide)/mean fluorescence without peptide. Background fluorescence without BB7.2 was subtracted for each individual value. $FI_{0.5}$ represents those peptide concentrations that increase HLA-A2.1 expression by 50% over the no peptide control and were calculated from the titration curves for each particular peptide.
Figure 1:
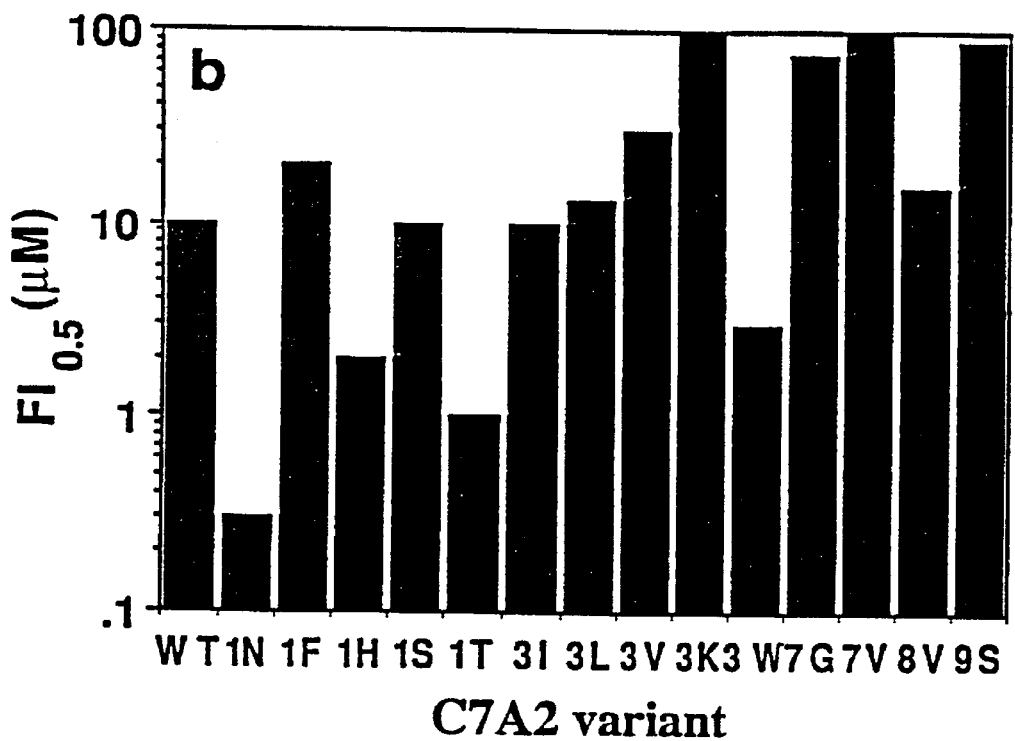
Figure 2:
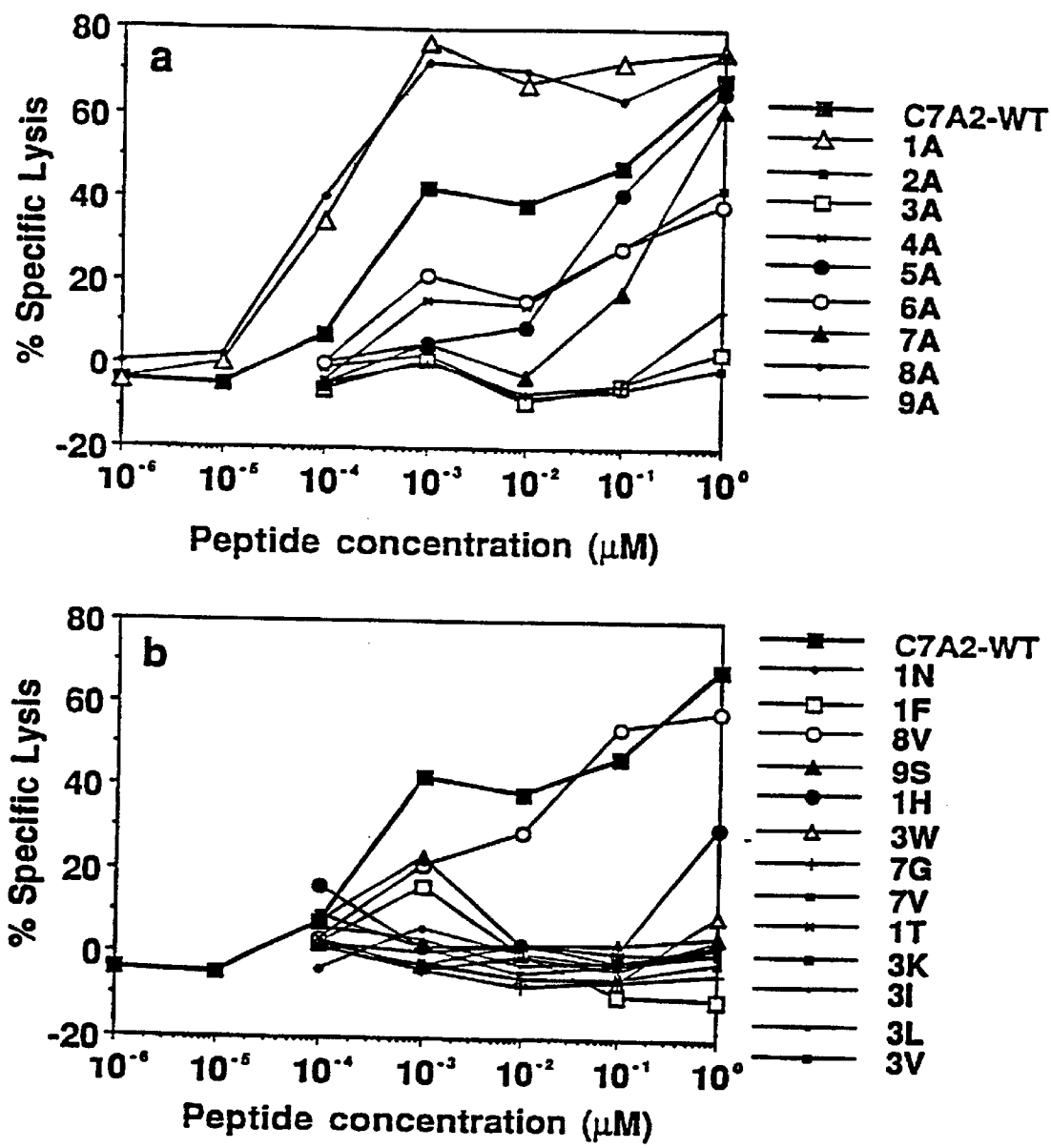
FIGS. 2A and 2B. Recognition of C7A2 Alanine (A) and non-Alanine (B)-substituted peptides by human CTL line ViT2, which is specific for C7A2 peptide presented by HLA-A2.1. C1R.A2.1 target cells were incubated for 2 h with $^{51}Cr$, washed three times and plated at 3000 cells per well in 96 well round bottom plates with different peptide concentrations. After 2 h, effector cells were added (E/T ratio: 5/1) and the plates were incubated for 4 h.
Figure 3:
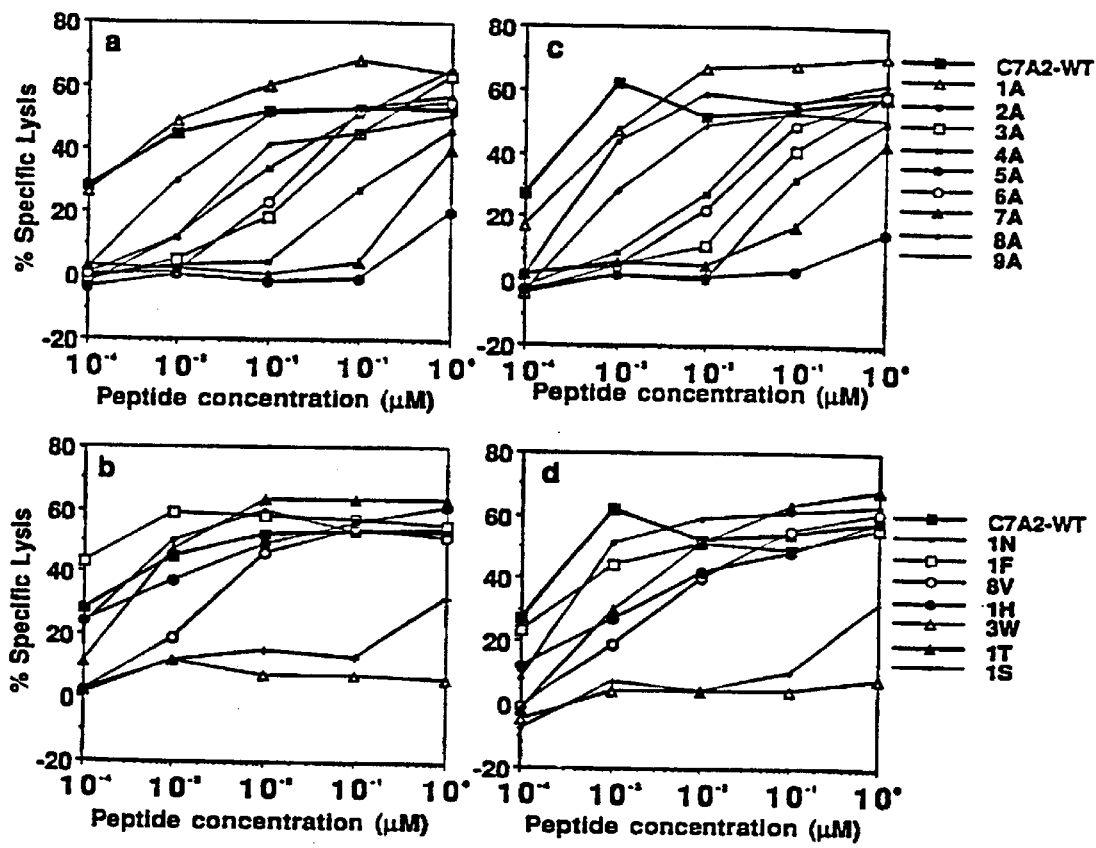
FIGS. 3A–D. Recognition of C7A2 Alanine (A,C) and non-Alanine (B,D)-substituted peptides by transgenic AAD mouse CTL lines AAD.10 (A,B) and AAD.1 (C,D) after 10–12 in vitro stimulations. C1R.AAD target cells were incubated for 2 h with $^{51}Cr$, washed three times and plated at 3000 cells per well in 96 well round bottom plates with different peptide concentrations. After 2 h, effector cells were added (E/T ratio: 10/1) and the plates were incubated for 4 h.
Figure 4:
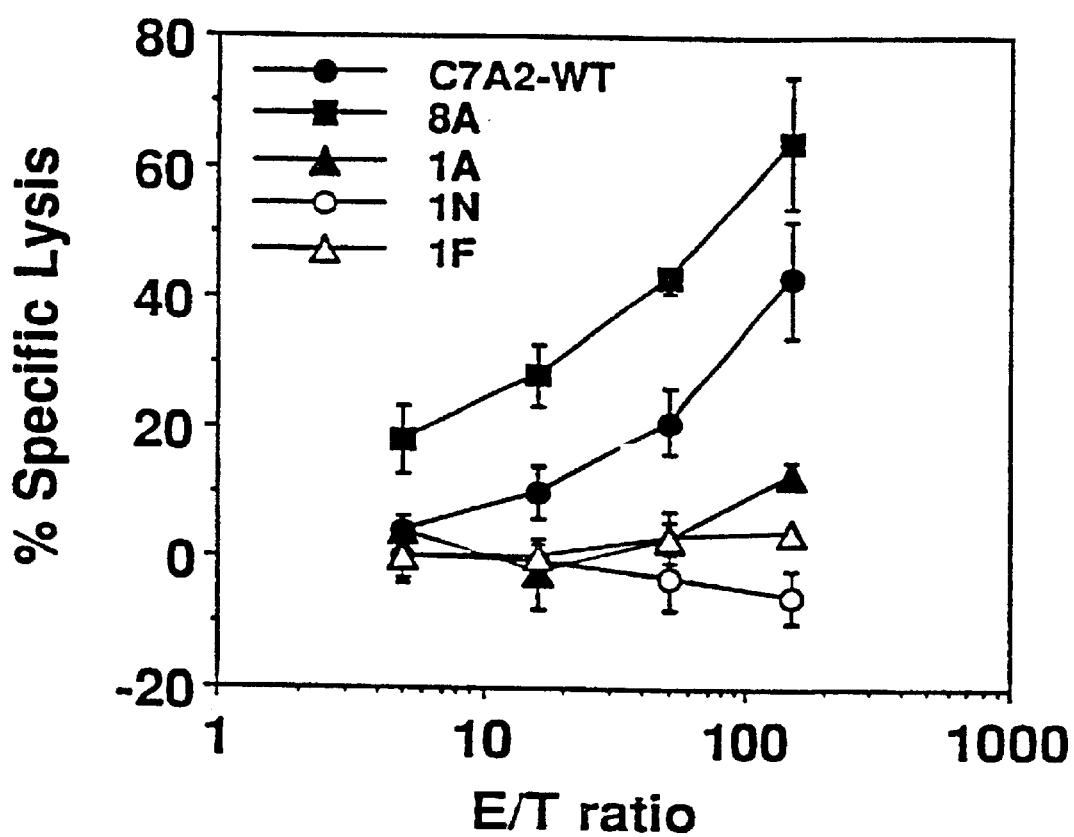
FIG. 4. Immunogenicity of C7A2-substituted peptides in AAD transgenic mice. Mice were immunized with 50 nmol CTL epitope plus 50 nmol HBVc 128–140 helper epitope and GM-CSF and IL-12 in IFA. Two weeks later, mice were boosted and 10–14 days after the boost, spleen cells were removed and stimulated in vitro with the CTL epitope. After one week of in vitro stimulation, a CTL assay was performed with target cells (AAD Con A blasts) incubated with or without 10 µM CTL peptide. CTL from each group were tested only with the peptide used to immunize those mice. Only results for peptide-pulsed target cells are shown. In all cases, percentage of specific lysis against peptide-unpulsed target cells was below 5%.
Figure 5:
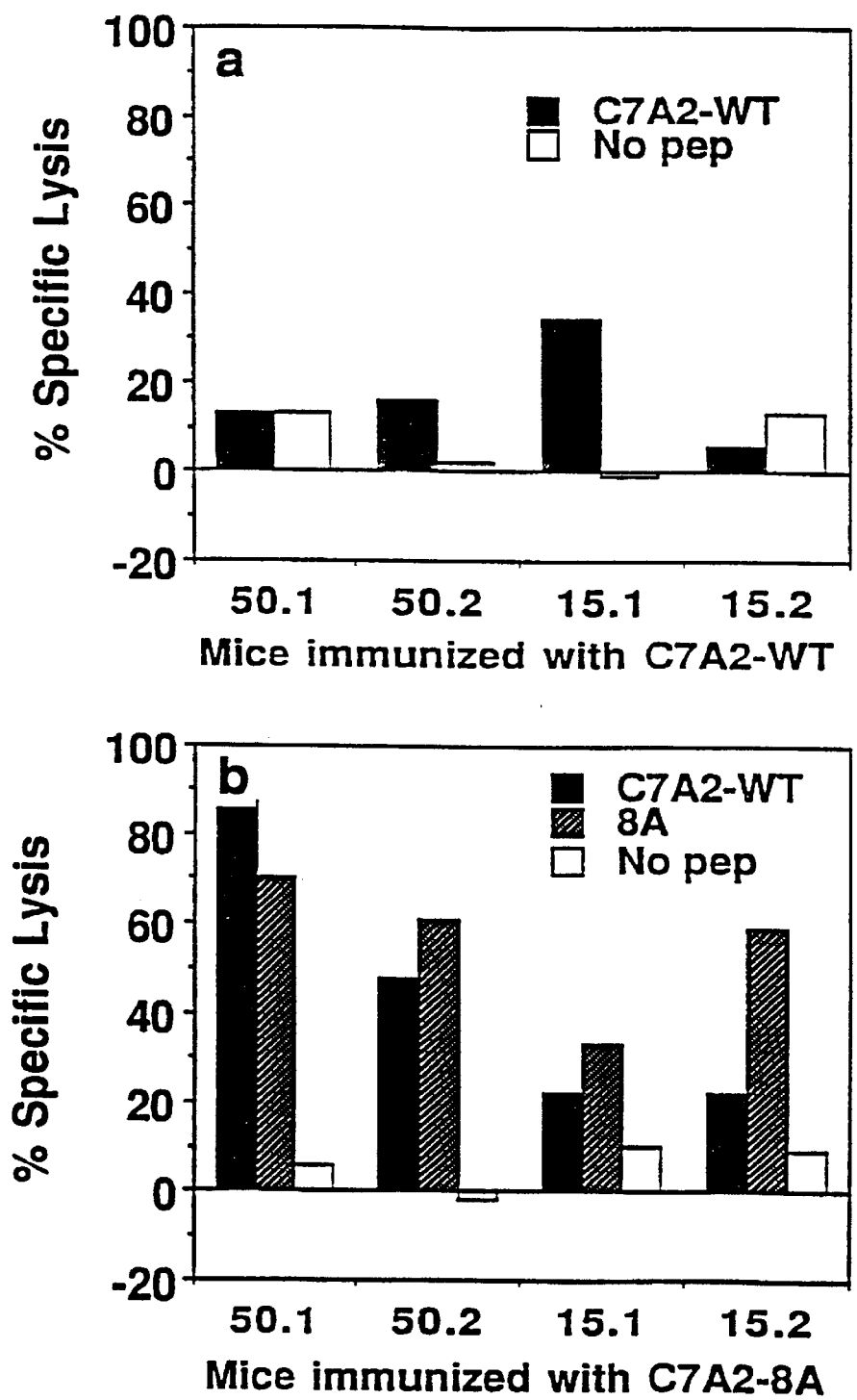
FIGS. 5A and 5B. Induction of CTL immune response against C7A2-WT in AAD transgenic mice using different C7A2 peptide variants. Mice were immunized with 50 or 15 nmol CTL epitope C7A2-WT (A) or 8A (B) plus 50 nmol HBVc 128–140 helper epitope and GM-CSF and IL-12 in IFA. Two weeks later, mice were boosted under the same conditions and 10–14 days after the boost, spleen cells were removed and stimulated in vitro with 10 μM CTL peptide-pulsed spleen cells. After two weeks of in vitro stimulation, a CTL assay was preformed with target cells (AAD Con A blasts) incubated with or without 10 μM peptide. The numbers 50.1 and 50.2, and 15.1 and 15.2 designate different mice immunized with 50 or 15 nmol CTL epitope respectively. (E/T ratio in the assay: 90/1).
Figure 6:
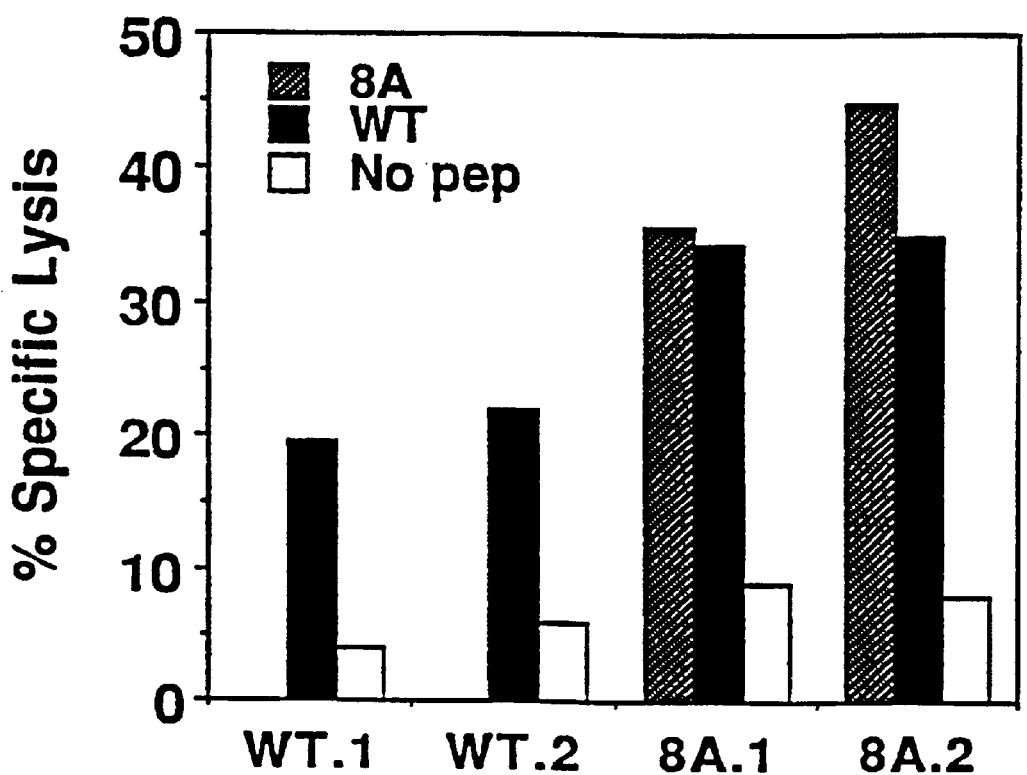
FIG. 6. Induction of CTL immune response against C7A2-WT in A2Kb transgenic mice using different C7A2 peptide variants. Mice were immunized with 50 nmol CTL epitope C7A2-WT or 8A plus 50 nmol HBVc 128–140 helper epitope in IFA. Two weeks later, mice were boosted under the same conditions and 10–14 days after the boost, spleen cells were removed and stimulated iii vitro with 10 μM CTL peptide-pulsed spleen cells. After two weeks of in vitro stimulation, a CTL assay was performed with target cells (A2Kb Con A blasts) incubated with or without 10 μM peptide. WT.1 and WT.2, and 8A.1 and 8A.2 designate different mice immunized with C7A2-WT and 8A CTL epitope respectively. (E/T ratio in the assay: 120/1 for WT.1 and WT.2; 70/1 for 8A.1 and 8A.2).

FIG. 7. Avidity of short term CTL lines induced with C7A2-WT and C7A2-8A.

AAD transgenic mice were immunized as described herein with 50 nmol CTL epitope C7A2-WT (solid lines) or C7A2-8A (dotted lines) plus 50 nmol HBVc 128–140 helper epitope and GM-CSF and IL-12 in IFA. Two weeks later, mice were boosted under the same conditions and 10–14 days after the boost, spleen cells were removed and stimulated in vitro with 10 μM CTL peptide-pulsed spleen cells. After 3–4 in vitro stimulation cycles, a CTL assay was performed with target cells (C1R.AAD) incubated with different peptide concentrations as indicated (circles, targets with C7A2-WT peptide; squares, targets with C7A2-8A peptide), at an E: T ratio of 10:1.

FIGS. 8A and 8B. Recognition of C7A2-derived peptides from different HCV genotypes by CTL induced following immunization with peptide 8A. AAD (A) and A2Kb (B) transgenic mice were immunized with 50 nmol CTL epitope 8A plus 50 nmol HBVc 128–140 helper epitope in IFA. Two weeks later, mice were boosted under the same conditions and 10–14 days after the boost, spleen cells were removed and stimulated in vitro with 10 μM CTL peptide-pulsed spleen cells. After two weeks of in vitro stimulation, a CTL assay was performed with target cells (Con A blasts) incubated with the different peptides at 10 μM. C7A2-WT has a sequence from HCV genotypes 1a, 1b and 3a, whereas peptide C7A2-8V has a sequence from genotypes 2a and 2b.

FIG. 9. Comparison of CTL activity at four weeks between AC7 30 μg and AC7-8A 30 μg, immunization to AAD mice. Target (T)=3000.

SUMMARY OF THE INVENTION

The present invention provides 1) an isolated peptide having the amino acid sequence DLMGYIPAV, (SEQ ID NO: 1); 2) an isolated HCV core polypeptide comprising an L→A substitution at amino acid position 139; 3) an isolated HCV core polypeptide having the amino acid sequence of SEQ ID NO: 2; and 4) a fragment of an HCV core polypeptide having fewer amino acids than the entire HCV core polypeptide and comprising the amino acid sequence of SEQ ID NO: 1. Also provided are nucleic acids which encode the peptides and polypeptides of this invention and vectors comprising the nucleic acids of this invention. These compositions can be present in a pharmaceutically acceptable carrier, which can also include a suitable adjuvant.

In addition, the present invention provides a method of producing an HCV core peptide having enhanced immunogenicity, comprising substituting one or more amino acids of the peptide having the amino acid sequence DLMGYIPLV (SEQ ID NO:3) and detecting enhanced immunogenicity of the substituted peptide as compared to the immunogenicity of a control peptide having the amino acid sequence of DLMGYIPLV (SEQ ID NO:3), whereby a substituted peptide having greater immunogenicity than the control peptide is a HCV core peptide having enhanced immunogenicity.

The present invention further provides methods of producing an immune response in a subject and treating or preventing HCV infection in a subject comprising administering to the subject, or to a cell of the subject, any of the compositions of this invention.

The present invention also provides a method of activating cytotoxic T lymphocytes, comprising contacting the lymphocytes with any of the peptides or polypeptides of this invention in the presence of a class I major histocompatibility complex molecule and also provides a composition comprising cytotoxic T lymphocytes activated by contact with the peptides or polypeptides of this invention in the presence of a class I major histocompatibility complex molecule.

Also provided are methods of detecting the presence of HCV core polypeptide in a cell comprising contacting the cell with the activated cytotoxic T lymphocytes of this invention under conditions whereby cytolysis of target cells can occur or cytokine production of the lymphocytes can occur and detecting cytolysis of target cells or cytokine production of the lymphocytes, whereby the detection of cytolysis of target cells or cytokine production of the lymphocytes indicates the presence of HCV core polypeptide in the cell.

In addition, the present invention provides a method of detecting hepatitis C virus in a sample comprising: a) contacting the sample with a cell which is susceptible to infection by hepatitis C virus under conditions whereby the cell can be infected by hepatitis C virus in the sample; b) contacting the cell of step (a) with the cytolytic T lymphocytes of this invention under conditions whereby cytolysis of target cells or cytokine production of the lymphocytes can occur; and c) detecting cytolysis of target cells or cytokine production of the lymphocytes, whereby the detection of cytolysis of target cells or cytokine production of the lymphocytes indicates the presence of hepatitis C virus in the sample.

The present invention further provides a method of diagnosing HCV infection in a subject comprising contacting cytotoxic T lymphocytes of the subject with the peptides or polypeptides of this invention in the presence of a class I major histocompatibility complex molecule under conditions whereby cytolysis of target cells or cytokine production of the lymphocytes can occur and detecting cytolysis of target cells or cytokine production of the lymphocytes, whereby the detection of cytolysis of target cells or cytokine production of the lymphocytes indicates a diagnosis of HCV infection in the subject.

Further provided are methods of determining a viral load of HCV in a subject comprising a) serially diluting a biological sample from the subject which contains hepatitis C virus; b) contacting each serially diluted sample with a cell which is susceptible to infection by hepatitis C virus under conditions whereby the cell can be infected by hepatitis C virus in the sample; c) contacting the cell of step (b) with the activated cytolytic T lymphocytes of this invention under conditions whereby cytolysis of target cells or cytokine production in the lymphocytes can occur; measuring the amount of cytolysis of target cells or cytokine production in the lymphocytes; comparing the amount of cytolysis of target cells or cytokine production in the lymphocytes with the amount of cytolysis of target cells or cytokine production by activated cytotoxic T lymphocytes contacted with cells infected with serially diluted control samples containing a known amount of hepatitis C virus; and determining the viral load of hepatitis C virus in the subject from the comparison with the samples of known amount.
Figure 7:
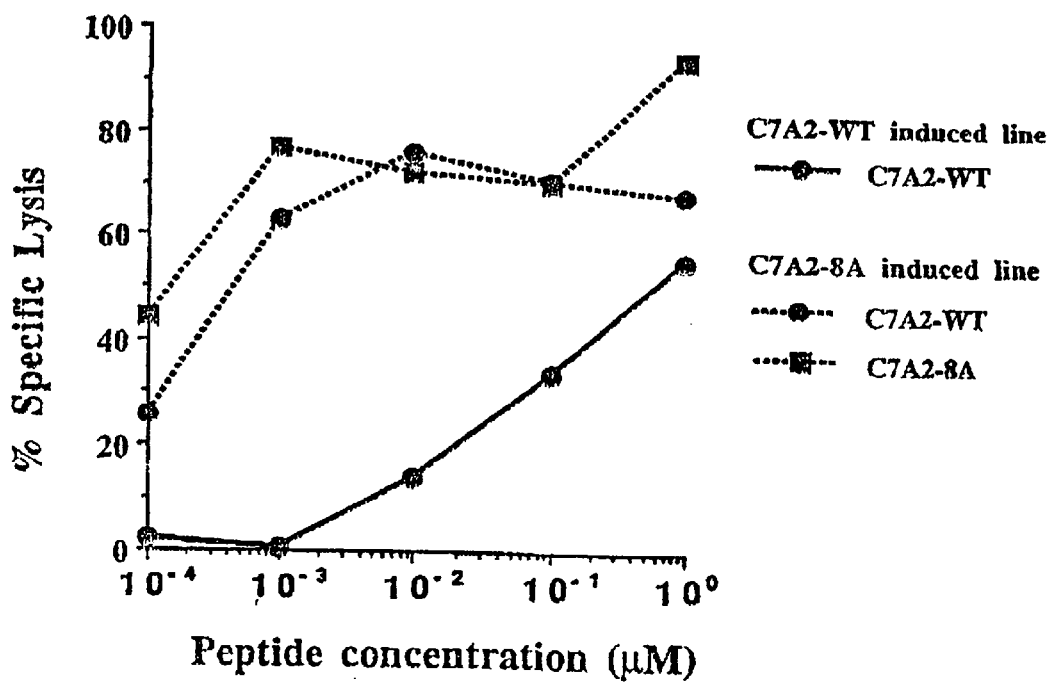
Figure 8:
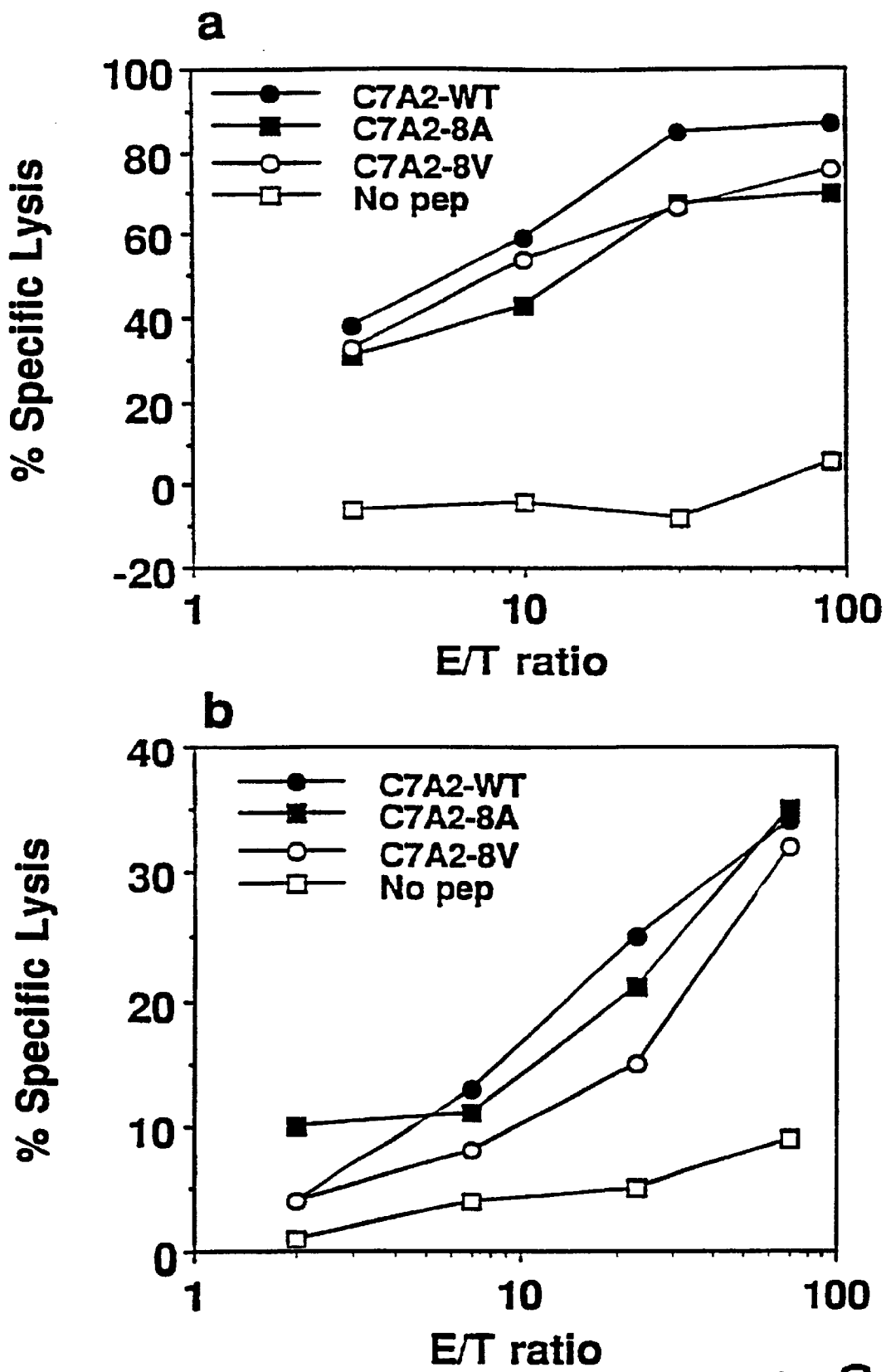
Figure 9:
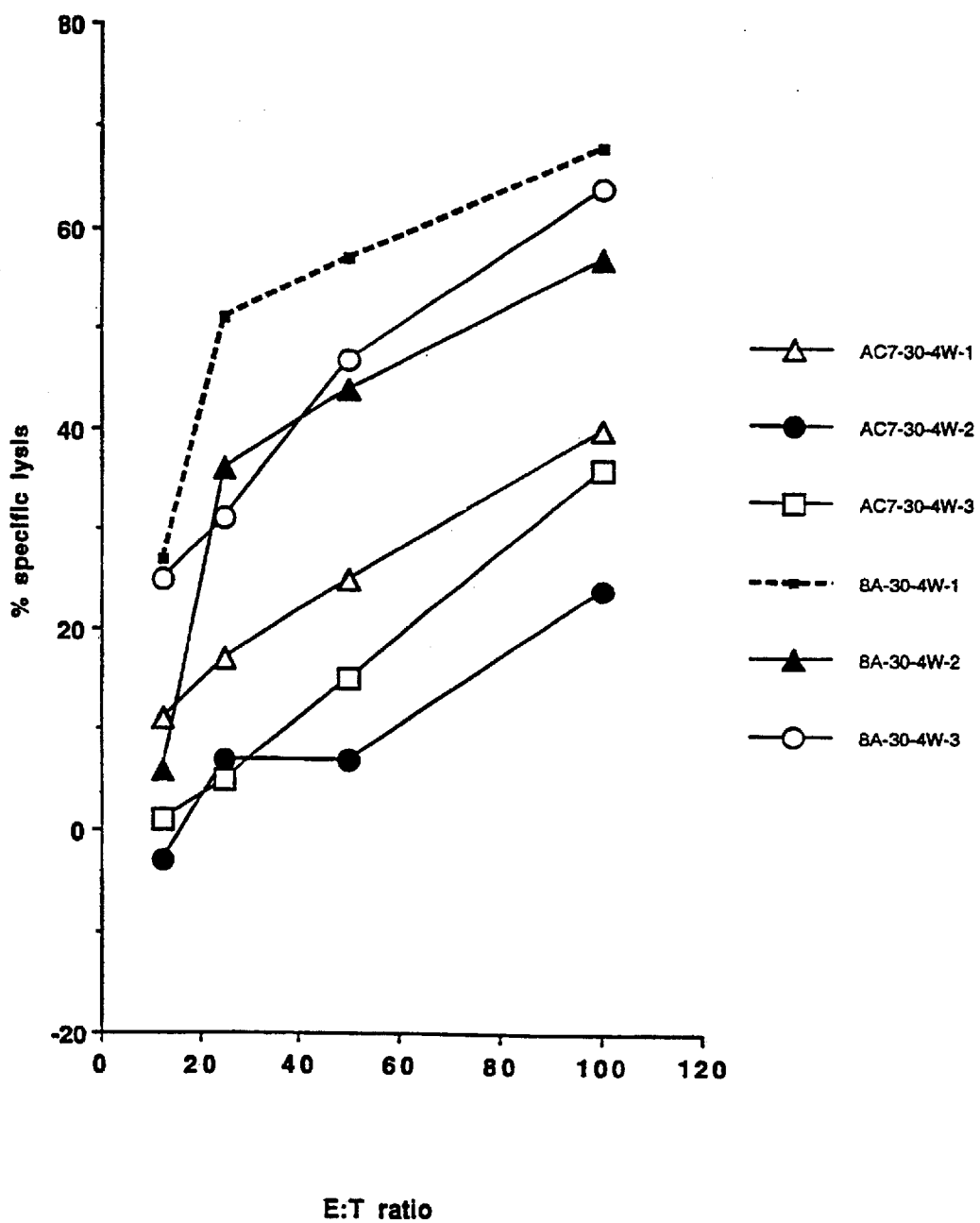

Finally, the present invention provides a method of determining the prognosis of a subject diagnosed with hepatitis C virus infection, comprising determining a viral load for the subject according to the methods of this invention, whereby a high viral load indicates a poor prognosis and a low viral load indicates a good prognosis.

Various other objectives and advantages of the present invention will become apparent from the following detailed description.

DETAILED DESCRIPTION OF THE INVENTION

As used herein, "a" or "an" may mean one or more. For example, "a" cell may mean one cell or more than one cell.

The present invention is based on the unexpected and surprising discovery, through the process of epitope enhancement, of an HCV core peptide having the amino acid sequence DLMGYIPAV (SEQ ID NO: 1), that has enhanced HLA-A2 binding affinity and CTL recognition in vitro and enhanced immunogenicity in vivo when compared to the naturally occurring peptide DLMGYIPLV (SEQ ID NO:3) at positions 132–140 in the HCV core polypeptide. Thus, the present invention provides an isolated peptide having the amino acid sequence of SEQ ID NO:1.

The present invention also provides an isolated HCV core polypeptide comprising an L→A substitution at amino acid position 139. Thus, the HCV core polypeptide of this invention can have the amino acid sequence of any of the variants of HCV now known or identified in the future and further comprise an L→A substitution at amino acid position 139 (see, e.g., ref. 87). Furthermore, the present invention provides an isolated HCV core polypeptide having the amino acid sequence of SEQ ID NO: 2.

Further, the present invention provides a polypeptide fragment of the HCV core polypeptide, having fewer amino acids than the HCV core polypeptide and comprising the amino acid sequence of SEQ ID NO: 1. Thus, the polypeptide fragment of this invention can comprise a sufficient number of contiguous amino acids to be identified as a polypeptide fragment of the HCV core polypeptide and including the amino acid sequence of SEQ ID NO:1, yet does not contain all of the amino acids of the HCV core polypeptide. For example, the entire HCV core polypeptide (SEQ ID NO:4) has 191 amino acids. Thus, the polypeptide fragment of this invention can have any number of amino acids fewer than 191 amino acids (e.g., 191-1, 191-5, 191-10, 191-50, 191-100, 191-130, 191-180 etc.) and having at least three amino acids which are contiguous amino acids of the HCV core polypeptide and would be recognized by one of ordinary skill in the art as contiguous amino acids of the HCV core polypeptide according to standard methods for identifying polypeptides and would also include the amino acid sequence of SEQ ID NO:1. The amino acid sequence of SEQ ID NO:1 can be present in the polypeptide fragment of this invention once or multiple times and can be at any position (e.g., N terminal, C terminal, internal) relative to the other amino acid sequence of the fragment.

"Isolated" as used herein means the peptide or polypeptide of this invention is sufficiently free of contaminants or cell components with which peptides or polypeptides normally occur and is present in such concentration as to be the only significant peptide or polypeptide present in the sample. "Isolated" does not mean that the preparation is technically pure (homogeneous), but it is sufficiently pure to provide the peptide or polypeptide in a form in which it can be used therapeutically.

"Epitope" as used herein means a specific amino acid sequence of limited length which, when present in the proper conformation, provides a reactive site for an antibody or T cell receptor. The identification of epitopes on antigens can be carried out by immunology protocols that are standard in the art (79).

Also as used herein, the terms peptide and polypeptide are used to describe a chain of amino acids which correspond to those encoded by a nucleic acid. A peptide usually describes a chain of amino acids of from two to about 30 amino acids and polypeptide usually describes a chain of amino acids having more than about 30 amino acids. The term polypeptide can refer to a linear chain of amino acids or it can refer to a chain of amino acids which have been processed and folded into a functional protein. It is understood, however, that 30 is an arbitrary number with regard to distinguishing peptides and polypeptides and the terms may be used interchangeably for a chain of armino acids around 30. The peptides and polypeptides of the present invention are obtained by isolation and purification of the peptides and polypeptides from cells where they are produced naturally or by expression of exogenous nucleic acid encoding the peptide or polypeptide. The peptides and polypeptides of this invention can be obtained by chemical synthesis, by proteolytic cleavage of a polypeptide and/or by synthesis from nucleic acid encoding the peptide or polypeptide.

The main discovery of this invention is a peptide or polypeptide having amino acid substitutions which enhance immunogenicity. Such substitutions can be made in the peptides and polypeptides of this invention by methods standard in the art and as set forth herein and enhanced immunogenicity can be determined according to the methods provided in the Examples herein. It is also understood that the peptides and polypeptides of this invention may also contain conservative substitutions where a naturally occurring amino acid is replaced by one having similar properties and which does not alter the function of the polypeptide. Such conservative substitutions are well known in the art. Thus, it is understood that, where desired, modifications and changes, which are distinct from the substitutions which enhance immunogenicity, may be made in the nucleic acid and/or amino acid sequence of the peptides and polypeptides of the present invention and still obtain a peptide or polypeptide having like or otherwise desirable characteristics. Such changes may occur in natural isolates or may be synthetically introduced using site-specific mutagenesis, the procedures for which, such as mis-match polymerase chain reaction (PCR), are well known in the art.

Moreover, the present invention provides isolated nucleic acids encoding each of the following: 1) the peptide having the amino acid sequence of SEQ ID NO:1; 2) the HCV core polypeptide having the amino acid sequence of SEQ ID NO:2; 3) the HCV core polypeptide comprising an L→A substitution at amino acid position 139; and 4) a fragment of the HCV core polypeptide having fewer amino acids than the entire HCV core polypeptide and comprising the peptide having the amino acid sequence of SEQ ID NO:1.

"Nucleic acid" as used herein refers to single- or double-stranded molecules which may be DNA, comprised of the nucleotide bases A, T, C and G, or RNA, omprised of the bases A, U (substitutes for T), C, and G. The nucleic acid may represent a coding strand or its complement. Nucleic acids may be identical in sequence to the sequence which is naturally occurring or may include alternative codons which encode the same amino acid as that which is found in the naturally occurring sequence. Furthermore, nucleic acids may include codons which represent conservative substitutions of amino acids as are well known in the art.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by techniques such as cell lysis followed by phenol plus chloroform extraction, followed by ethanol precipitation of the nucleic acids (80). The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

The nucleic acid encoding the peptide or polypeptide of this invention can be part of a recombinant nucleic acid construct comprising any combination of restriction sites and/or functional elements as are well known in the art which facilitate molecular cloning and other recombinant DNA manipulations. Thus, the present invention further provides a recombinant nucleic acid construct comprising a nucleic acid encoding a peptide and/or polypeptide of this invention.

The present invention further provides a vector comprising a nucleic acid encoding a peptide and/or polypeptide of this invention. The vector can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols. The expression vector can comprise viral nucleic acid including, but not limited to, vaccinia virus, adenovirus, retrovirus and/or adeno-associated virus nucleic acid. The nucleic acid or vector of this invention can also be in a liposome or a delivery vehicle which can be taken up by a cell via receptor-mediated or other type of endocytosis.

The nucleic acid of this invention can be in a cell, which can be a cell expressing the nucleic acid whereby a peptide and/or polypeptide of this invention is produced in the cell. In addition, the vector of this invention can be in a cell, which can be a cell expressing the nucleic acid of the vector whereby a peptide and/or polypeptide of this invention is produced in the cell. It is also contemplated that the nucleic acids and/or vectors of this invention can be present in a host animal (e.g., a transgenic animal) which expresses the nucleic acids of this invention and produces the peptides and/or polypeptides of this invention.

The nucleic acid encoding the peptides and polypeptides of this invention can be any nucleic acid that functionally encodes the peptides and polypeptides of this invention. To functionally encode the peptides and polypeptides (i.e., allow the nucleic acids to be expressed), the nucleic acid of this invention can include, for example, expression control sequences, such as an origin of replication, a promoter, an enhancer and necessary information processing sites, such as ribosome binding sites, RNA splice sites, polyadenylation sites and transcriptional terminator sequences.

Preferred expression control sequences are promoters derived from metallothionine genes, actin genes, immunoglobulin genes, CMV, SV40, adenovirus, bovine papilloma virus, etc. A nucleic acid encoding a selected peptide or polypeptide can readily be determined based upon the genetic code for the amino acid sequence of the selected peptide or polypeptide and many nucleic acids will encode any selected peptide or polypeptide. Modifications in the nucleic acid sequence encoding the peptide or polypeptide are also contemplated. Modifications that can be useful are modifications to the sequences controlling expression of the peptide or polypeptide to make production of the peptide or polypeptide inducible or repressible as controlled by the appropriate inducer or repressor. Such methods are standard in the art (81). The nucleic acid of this invention can be generated by means standard in the art, such as by recombinant nucleic acid techniques and by synthetic nucleic acid synthesis or in vitro enzymatic synthesis.

The present invention further provides a method of producing an HCV core peptide having enhanced immunogenicity, comprising substituting one or more amino acids of the peptide having amino acid sequence DLMGYIPLV (SEQ ID NO:3) and detecting enhanced immunogenicity of the substituted peptide as compared to the immunogenicity of a control peptide having the amino acid sequence of DLMGYIPLV (SEQ ID NO:3), whereby a substituted peptide having greater immunogenicity than the control peptide is an HCV core peptide having enhanced immunogenicity. Immunogenicity of the substituted and control peptide is determined according to the methods set forth in the Examples provided herein. The production of the peptide having the amino acid sequence of SEQ ID NO:3 and the substituted peptides of this invention can be carried out according to methods standard in the art for peptide synthesis. Alternatively, a nucleic acid encoding the amino acid sequence of SEQ ID NO:3 or encoding a substituted peptide of interest can be synthesized according to standard nucleic acid synthesis protocols and the nucleic acid can be expressed according to methods well known for expression of nucleic acid. The resulting peptide can then be removed from the expression system by standard isolation and purification procedures and tested for immunogenicity as taught herein.

On the basis of the discovery of this invention, substitution of an amino acid or amino acids of the peptide DLMGYIPLV (SEQ ID NO:3) to produce a peptide of this invention having enhanced immunogenicity as determined by the methods of this invention, can be carried out by a systematic approach comprising replacement of each of the amino acids in the peptide sequentially, starting from the amino terminus of the peptide. Peptides having a single amino acid substitution which show enhanced immunogenicity by the methods described herein can be identified and a second amino acid substitution can be introduced into the amino acid sequence of the singly-substituted peptide sequentially, starting from the amino terminus of the singly-substituted peptide. These doubly-substituted peptides can then be tested for enhanced immunogenicity and those which show such enhancement can have further amino acid substitutions made by the systematic, sequential method described herein. Thus, any combination of substitutions can be tested for enhanced immunogenicity in a systematic manner.

The present invention also provides a method for producing the peptides and polypeptides of this invention comprising producing the cells of this invention which contain the nucleic acids or vectors of this invention as exogenous nucleic acid; culturing the cells under conditions whereby the exogenous nucleic acid in the cell can be expressed and the encoded peptide and/or polypeptide can be produced; and isolating the peptide and/or polypeptide from the cell. Thus, it is contemplated that the peptides and polypeptides of this invention can be produced in quantity ill vitro in either prokaryotic or eukaryotic expression systems as are well known in the art.

For expression in a prokaryotic system, there are numerous *E. coli* (*Escherichia coli*) expression vectors known to one of ordinary skill in the art useful for the expression of nucleic acid which encodes peptides or polypeptides. Other microbial hosts suitable for use include bacilli, such as *Bacillus subtilis,* and other enterobacteria, such as Salmonella, Serratia, as well as various Pseuidomonas species. These prokaryotic hosts can support expression vectors which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence and have ribosome binding site sequences for example, for initiating and completing transcription and translation. If necessary, an amino terminal methionine can be provided by insertion of a Met codon 5' and in-frame with the polypeptide. Also, the carboxy-terminal extension of the polypeptide can be removed using standard oligonucleotide mutagenesis procedures.

The nucleic acid sequences can be expressed in hosts after the sequences have been positioned to ensure the functioning of an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired nucleic acid sequences (82).

For eukaryotic system expression, a yeast expression system can be used. There are several advantages to yeast expression systems. First, evidence exists that polypeptides produced in a yeast expression system exhibit correct disulfide pairing. Second, post-translational glycosylation is efficiently carried out by yeast expression systems. The *Saccharomyces cerevisiae* pre-pro-alpha-factor leader region (encoded by the MFα-1 gene) is routinely used to direct protein secretion from yeast (83). The leader region of pre-pro-alpha-factor contains a signal peptide and a pro-segment which includes a recognition sequence for a yeast protease encoded by the KEX2 gene. This enzyme cleaves the precursor protein on the carboxyl side of a Lys-Arg dipeptide cleavage-signal sequence. The polypeptide coding sequence can be fused in-frame to the pre-pro-alpha-factor leader region. This construct is then put under the control of a strong transcription promoter, such as the alcohol dehydrogenase I promoter or a glycolytic promoter. The coding sequence is followed by a translation termination codon, which is followed by transcription termination signals. Alternatively, the coding sequence of interest can be fused to a second polypeptide coding sequence, such as Sj26 or β-galactosidase, used to facilitate purification of the resulting fusion polypeptide by affinity chromatography. The insertion of protease cleavage sites to separate the components of the fusion polypeptide is applicable to constructs used for expression in yeast.

Efficient post-translational glycosylation and expression of recombinant polypeptides can also be achieved in Baculovirus systems in insect cells, as are well known in the art.

The peptides and polypeptides of this invention can also be expressed in mammalian cells. Mammalian cells permit the expression of peptides and polypeptides in an environment that favors important post-translational modifications such as folding and cysteine pairing, addition of complex carbohydrate structures and secretion of active protein. Vectors useful for the expression of peptides and polypeptides in mammalian cells are characterized by insertion of the coding sequence between a strong viral promoter and a polyadenylation signal. The vectors can contain genes conferring either gentamicin or methotrexate resistance for use as selectable markers. For example, the coding sequence can be introduced into a Chinese hamster ovary (CHO) cell line using a methotrexate resistance-encoding vector. Presence of the vector RNA in transformed cells can be confirmed by Northern blot analysis and production of a cDNA or opposite strand RNA corresponding to the peptide or polypeptide coding sequence can be confirmed by Southern and Northern blot analysis, respectively. A number of other suitable host cell lines capable of producing exogenous peptides and polypeptides have been developed in the art and include the CHO cell lines, HeLa cells, myeloma cell lines, Jurkat cells and the like. Expression vectors for these cells can include expression control sequences, as described above.

The nucleic acids and/or vectors of this invention can be transferred into the host cell by well-known methods, which vary depending on the type of cell host. For example, calcium chloride transfection is commonly utilized for prokaryotic cells, whereas calcium phosphate treatment or electroporation may be used for other cell hosts.

The peptides, polypeptides, nucleic acids, vectors and cells of this invention can be present in a pharmaceutically acceptable carrier. Thus, the present invention provides a composition comprising 1) a peptide having the amino acid sequence of SEQ ID NO: 1; 2) an HCV core polypeptide comprising an L→A substitution at amino acid position 139; 3) an HCV core polypeptide having the amino acid sequence of SEQ ID NO:2; 4) a fragment of an HCV core polypeptide having fewer amino acids than the entire HCV core polypeptide and comprising the amino acid sequence of SEQ ID NO:1; 5) a nucleic acid encoding any of the peptides or polypeptides of this invention; 6) a vector comprising any of the nucleic acids of this invention; and/or 7) a cell comprising any of the nucleic acids and/or vectors of this invention, in a pharmaceutically acceptable carrier. By "pharmaceutically acceptable" is meant a material that is not biologically or otherwise undesirable, i.e., the material may be administered to an individual along with the selected peptide, polypeptide, nucleic acid, vector or cell without causing substantial deleterious biological effects or interacting in a deleterious manner with any of the other components of the composition in which it is contained.

Furthermore, any of the compositions of this invention can comprise a pharmaceutically acceptable carrier and a suitable adjuvant. As used herein, "suitable adjuvant" describes an adjuvant capable of being combined with the peptide or polypeptide of this invention to further enhance an immune response without deleterious effect on the subject or the cell of the subject. A suitable adjuvant can be, but is not limited to, MONTANIDE ISA51 (Seppic, Inc., Fairfield, N.J.), SYNTEX adjuvant formulation 1 (SAF-1), composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Other suitable adjuvants are well known in the art and include QS-21, Freund's adjuvant (complete and incomplete), alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

The compositions of the present invention can also include other medicinal agents, pharmaceutical agents, carriers, diluents, immunostimulatory cytokines, etc. Actual methods of preparing such dosage forms are known, or will be apparent, to those skilled in this art (84).

It is contemplated that the above-described compositions of this invention can be administered to a subject or to a cell of a subject to impart a therapeutic benefit. Thus, the present invention further provides a method of producing an immune response in an immune cell of a subject, comprising contacting the cell with 1) a peptide having the amino acid sequence of SEQ ID NO:1; 2) an HCV core polypeptide having the amino acid sequence of SEQ ID NO:2; 3) an HCV core polypeptide comprising an L→A substitution at amino acid position 139; 4) a fragment of the HCV core polypeptide having fewer amino acids than a complete HCV core polypeptide and comprising SEQ ID NO:1; 5) a nucleic acid encoding any of the peptides or polypeptides of this invention and/or 6) a vector comprising any one of the nucleic acids of this invention. The cell can be in vivo or ex vivo and can be, but is not limited to a CD8+ T lymphocyte (e.g., a cytotoxic T lymphocyte) or an MHC I-expressing antigen presenting cell, such as a dendritic cell, a macrophage or a monocyte.

The present invention additionally provides a method of producing an immune response in a subject by administering to the subject any of the compositions of this invention, including a composition comprising a pharmaceutically acceptable carrier and 1) a peptide having the amino acid sequence of SEQ ID NO:1; 2) an HCV core polypeptide having the amino acid sequence of SEQ ID NO:2; 3) an HCV core polypeptide comprising an L→A substitution at amino acid position 139; 4) a fragment of the HCV core polypeptide having fewer amino acids than a complete HCV core polypeptide and comprising SEQ ID NO:1; 5) a nucleic acid encoding any of the peptides or polypeptides of this invention and/or 6) a vector comprising any one of the nucleic acids of this invention. The composition can further comprise a suitable adjuvant, as set forth herein.

Detection of an immune response in the subject or in the cells of the subject can be carried out according to the methods set forth in the Examples provided herein, such as for detecting the presence of cytotoxic T cells activated by the peptides or polypeptides of this invention.

In addition, the present invention provides a method of treating or preventing HCV infection in a subject comprising contacting an immune cell of the subject with any of the peptide, polypeptide, fragments, nucleic acids vectors and/or cells of this invention. The cell can be ill vivo or ex vivo and can be a CD8+ T cell which is contacted with the peptide or polypeptide of this invention in the presence of a class I MHC molecule, which can be a soluble molecule or it can be present on the surface of a cell which expresses class I MHC molecules. The cell can also be an antigen presenting cell or other class I MHC-expressing cell which can be contacted with the nucleic acids and/or vectors of this invention under conditions whereby the nucleic acid or vector is introduced into the cell by standard methods for uptake of nucleic acid and vectors. The nucleic acid encoding the peptide or polypeptide of this invention is then expressed and the peptide or polypeptide product is processed within the antigen presenting cell or other MHC I-expressing cell and presented on the cell surface as an MHC I/antigen complex, The antigen presenting cell or other class I MHC-expressing cell is then contacted with an immune cell of the subject which binds the class I MHC/antigen complex and elicits an immune response which treats or prevents HCV infection in the subject.

The present invention also provides a method of treating or preventing HCV infection in a subject, comprising administering to the subject any of the compositions of this invention, including a composition comprising a pharmaceutically acceptable carrier and 1) a peptide having the amino acid sequence of SEQ ID NO:1; 2) an HCV core polypeptide having the amino acid sequence of SEQ ID NO:2; 3) an HCV core polypeptide comprising an L→A substitution at amino acid position 139; 4) a fragment of the HCV core polypeptide having fewer amino acids than a complete HCV core polypeptide and comprising SEQ ID NO:1; 5) a nucleic acid encoding any of the peptides or polypeptides of this invention and/or 6) a vector comprising any one of the nucleic acids of this invention.

As set forth above, it is contemplated that in the methods wherein the compositions of this invention are administered to a subject or to a cell of a subject, such methods can further comprise the step of administering a suitable adjuvant to the subject or to a cell of the subject. The adjuvant can be in the composition of this invention or the adjuvant can be in a separate composition comprising the suitable adjuvant and a pharmaceutically acceptable carrier. The adjuvant can be administered prior to, simultaneous with or after administration of the composition containing any of the peptides, polypeptides, nucleic acids and/or vectors of this invention. For example, QS-21, similar to alum, complete Freund's adjuvant, SAF, etc., can be administered within hours (before or after) of administration of the peptide. The effectiveness of an adjuvant can be determined by measuring the immune response directed against the peptide or polypeptide of this invention with and without the adjuvant, using standard procedures, as described in the Examples herein.

The subject of this invention can be any subject in need of the immune response of this invention and/or in need of treatment for or prevention from HCV infection. Symptoms of HCV infection can include low-grade fever, malaise and anorexia. Elevation of serum liver enzymes such as SGOT and SGPT is also typically found. The diagnosis of HCV infection can be made by detecting HCV antibodies in the subject's serum. Confirmation of the diagnosis can be made by PCR assay of the subject's blood for HCV RNA. It would also be well understood in the art that many subjects infected with HCV are asymptomatic.

Common sources of infection can include blood transfusions, infected sexual partners and contaminated needles. Further, subjects vulnerable to blood-borne disease can be at risk for HCV infection. Thus, a subject for whom the methods of this invention would be indicated for preventing HCV infection can be a subject who has received a blood transfusion, has an infected sexual partner, shares contaminated needles for intravenous drug abuse or has been accidentally stuck with a contaminated needle or exposed to HCV-contaminated tissues or body fluids (e.g., a health care worker).

The peptides and polypeptides of this invention can be administered to a cell of a subject either in vivo or ex vivo. For administration to a cell of the subject in vivo, as well as for administration to the subject, the peptides and polypeptides of this invention can be administered orally, parenterally (e.g., intravenously), by intramuscular injection, by intraperitoneal injection, subcutaneous injection, transdermally, extracorporeally, topically or the like. Also, the peptide or polypeptide of this invention may be pulsed onto dendritic cells which are isolated or grown from patient cells, according to methods well known in the art, or onto bulk PBMC or various cell subfractions thereof from a patient.

The exact amount of the peptide or polypeptide required will vary from subject to subject, depending on the species, age, weight and general condition of the subject, the particular peptide or polypeptide used, its mode of administration and the like. Thus, it is not possible to specify an exact amount for every peptide or polypeptide. However, an appropriate amount can be determined by one of ordinary skill in the art using only routine experimentation given the teachings herein (84).

As an example, to a subject diagnosed with HCV infection or known to be at risk of being infected by HCV, between about 50–1000 nM and more preferably, between about 100–500 nM of a peptide and/or polypeptide of this invention can be administered subcutaneously and can be in an adjuvant, at one to three week intervals for approximately 12 weeks or until an evaluation of the subject's clinical parameters (symptoms, liver enzyme levels, HCV RNA levels) indicate that the subject is not infected by HCV. Alternatively, a peptide and/or polypeptide of this invention can be pulsed onto dendritic cells at a concentration of between about 10–100 μM and the dendritic cells can be administered to the subject intravenously at the same time intervals. The treatment can be continued or resumed if the subject's clinical parameters indicate that HCV infection is present and can be maintained until the infection is no longer detected by these parameters.

If ex vivo methods are employed, cells or tissues can be removed and maintained outside the subject's body according to standard protocols well known in the art. The peptides or polypeptides of this invention can be introduced into the cells via known mechanisms for uptake of peptides and polypeptides into cells (e.g., phagocytosis, pulsing onto class I MHC-expressing cells, liposomes, etc.). The cells can then be infused (e.g., in a pharmaceutically acceptable carrier) or transplanted back into the subject per standard methods for the cell or tissue type. Standard methods are known for transplantation or infusion of various cells into a subject.

The nucleic acids and vectors of this invention can also be administered to a cell of the subject either in vivo or ex vivo.

The cell can be any cell which can take up and express exogenous nucleic acid and produce the peptides and polypeptides of this invention. Thus, the peptides and polypeptides of this invention can be produced by a cell which secretes them, whereby the peptide or polypeptide is produced and secreted and then taken up and subsequently processed by an antigen presenting cell or other class I MHC-expressing cell and presented to the immune system for induction of an immune response. Alternatively, the peptides and polypeptides of this invention can be directly produced in an antigen presenting cell or other class I MHC-expressing cell in which the peptide or polypeptide can be produced and processed directly and presented to the immune system on the cell surface.

The nucleic acids and vectors of this invention can be administered orally, parenterally (e.g., intravenously), by intramuscular injection, by intraperitoneal injection, transdermally, extracorporeally, topically or the like. In the methods described herein which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for expression of the peptides or polypeptides of this invention. The vector can be a commercially available preparation or can be constructed in the laboratory according to methods well known in the art.

Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., 70,71). The recombinant retrovirus can then be used to infect and thereby deliver to the infected cells nucleic acid encoding the peptide or polypeptide. The exact method of introducing the exogenous nucleic acid into mammalian cells is, of course, not limited to the use of retroviral vectors. Other techniques are widely available for this procedure including the use of adenoviral vectors (72), adeno-associated viral (AAV) vectors (73), lentiviral vectors (74), pseudotyped retroviral vectors (75) and vaccinia viral vectors (85), as well as any other viral vectors now known or developed in the future. Physical transduction techniques can also be used, such as liposome delivery and receptor-mediated and other endocytosis mechanisms (see, for example, 76). This invention can be used in conjunction with any of these or other commonly used gene transfer methods.

As one example, if the nucleic acid of this invention is delivered to the cells of a subject in an adenovirus vector, the dosage for administration of adenovirus to humans can range from about $10^7$ to $10^9$ plaque forming units (pfu) per injection, but can be as high as $10^{12}$ pfu per injection (77,78). Ideally, a subject will receive a single injection. If additional injections are necessary, they can be repeated at six month intervals for an indefinite period and/or until the efficacy of the treatment has been established. As set forth herein, the efficacy of treatment can be determined by evaluating the clinical parameters described herein.

The exact amount of the nucleic acid or vector required will vary from subject to subject, depending on the species, age, weight and general condition of the subject, the particular nucleic acid or vector used, its mode of administration and the like. Thus, it is not possible to specify an exact amount for every nucleic acid or vector. However, an appropriate amount can be determined by one of ordinary skill in the art using only routine experimentation given the teachings herein (84).

If ex vivo methods are employed, cells or tissues can be removed and maintained outside the body according to standard protocols well known in the art. The nucleic acids and vectors of this invention can be introduced into the cells via any gene transfer mechanism, such as, for example, virus-mediated gene delivery, calcium phosphate mediated gene delivery, electroporation, microinjection or proteoliposomes. The transduced cells can then be infused (e.g., in a pharmaceutically acceptable carrier) or transplanted back into the subject per standard methods for the cell or tissue type. Standard methods are known for transplantation or infusion of various cells into a subject.

Parenteral administration of the peptides, polypeptides, nucleic acids and/or vectors of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, subcutaneous, intramuscular, intraperitoneal, intravenous and intratracheal routes. A more recently revised approach for parenteral administration involves use of a slow release or sustained release system such that a constant dosage is maintained. See, e.g., U.S. Pat. No. 3,610,795, which is incorporated by reference herein.

The efficacy of treating or preventing HCV infection by the methods of the present invention can be determined by detecting a clinical improvement of the subject's symptoms, as would be well known to one of skill in the art. Moreover, a decrease in the serum levels of liver enzymes such as SGOT and SGPT, as well as a decrease in viral RNA as determined by PCR assay can provide objective evidence of the efficacy of these methods.

The present invention additionally provides a method of activating a cytotoxic T lymphocyte comprising contacting the lymphocyte with any of the peptides and/or polypeptides of this invention in the presence of a class I MHC molecule. The class I MHC molecule can be produced in soluble form according to methods standard in the art or it can be on the surface of a cell which expresses class I MHC. The conditions under which the CTL are contacted with the peptides and/or polypeptides in the presence of the class I MHC molecule in order to activate the CTL are well known in the art and are described in the Examples provided herein. Examples of cells which express class I MHC molecules include, but are not limited to, dendritic cells, monocytes, macrophages, fibroblasts, B lymphocytes and T lymphocytes. Cytotoxic T lymphocyte cell lines can be obtained according to the methods set forth in the Examples provided herein. Activation of the CTL can be determined according to the methods set forth in the Examples provided herein.

Thus, the present invention further provides a composition comprising cytotoxic T lymphocytes activated by contact with any of the peptides and/or polypeptides of this invention in the presence of a class I MHC molecule. It would be understood that the composition can comprise a population of PBMC which includes activated CTL or the composition can comprise a CTL line, as described in the Examples provided herein.

It is further contemplated that the compositions of the present invention can be used in diagnostic and therapeutic applications. Thus, the present invention provides a method of detecting the presence of hepatitis C virus core polypeptide in a cell, comprising contacting the cell with the activated cytotoxic T lymphocytes of this invention under conditions whereby cytolysis of target cells can occur and detecting cytolysis of target cells, whereby the detection of cytolysis of target cells indicates the presence of hepatitis C virus core polypeptide in the cell. The cell can be any cell which can maintain infection by HCV and be recognized by the activated CTL of this invention.

A method of detecting the presence of hepatitis C virus core polypeptide in a cell is also provided, comprising contacting the cell with the activated cytotoxic T lymphocytes of this invention under conditions whereby cytokine production in the lymphocytes can occur and detecting cytokine production in the lymphocytes, whereby the detection of cytokine production in the lymphocytes indicates the presence of hepatitis C virus core polypeptide in the cell. The cell can be any cell which can maintain infection by HCV and be recognized by the activated CTL of this invention.

Also provided herein is a method of detecting hepatitis C virus in a sample, comprising: a) contacting the sample with a cell which is susceptible to infection by hepatitis C virus under conditions whereby the cell can be infected by hepatitis C virus in the sample; b) contacting the cell of step (a) with the cytolytic T lymphocytes of this invention under conditions whereby cytolysis of target cells can occur; and c) detecting cytolysis of target cells, whereby the detection of cytolysis of target cells indicates the presence of hepatitis C virus in the sample.

The sample of this invention can be any sample in which infectious HCV can be present. For example, the sample can be a sample removed from a subject, such as a body fluid, cells or tissue which can contain infectious HCV particles.

Furthermore, the present invention provides a method of detecting hepatitis C virus in a sample comprising: a) contacting the sample with a cell which is susceptible to infection by hepatitis C virus under conditions whereby the cell can be infected by hepatitis C virus in the sample; b) contacting the cell of step (a) with the cytolytic T lymphocytes of this invention under conditions whereby cytokine production can occur in the lymphocytes; and c) detecting cytokine production in the lymphocytes, whereby the detection of cytokine production in the lymphocytes indicates the presence of hepatitis C virus in the sample.

Additionally, the present invention provides a method of diagnosing hepatitis C virus infection in a subject comprising contacting cytotoxic T lymphocytes of the subject with any of the peptides or polypeptides of this invention in the presence of a class I MHC molecule under conditions whereby cytolysis of target cells can occur and detecting cytolysis of target cells, whereby the detection of cytolysis of target cells indicates a diagnosis of hepatitis C virus infection in the subject.

A method of diagnosing hepatitis C virus infection in a subject is further provided, comprising contacting cytotoxic T lymphocytes of the subject with any of the peptides or polypeptides of this invention under conditions whereby cytokine production in the CTL can occur and detecting cytokine production in the CTL, whereby the detection of cytokine production in the CTL indicates a diagnosis of hepatitis C virus infection in the subject.

Cytotoxic T lymphocytes can be obtained from the subject as described in the Examples set forth herein. The subject of this invention can be any animal which is susceptible to infection by HCV. For example, the subject can be a chimpanzee and in a preferred embodiment, the subject is a human.

The present invention also provides a method of determining a viral load of hepatitis C virus in a subject comprising: a) serially diluting a biological sample from the subject which contains hepatitis C virus; b) contacting each serially diluted sample with a cell which is susceptible to infection by hepatitis C virus under conditions whereby the cell can be infected by hepatitis C virus in the sample; c) contacting the cell of step (b) with the cytolytic T lymphocytes of this invention under conditions whereby cytokine production can occur in the CTL; d) measuring the amount of cytokine production in the CTL; e) comparing the amount of cytokine production in the CTL of step (c) with the amount of cytokine production in activated CTL contacted with cells infected with serially diluted control samples containing a known amount of hepatitis C virus; and f) determining the viral load of hepatitis C virus in the subject from the comparison of step (e).

An additional method is provided, of determining a viral load of hepatitis C virus in a subject comprising: a) serially diluting a biological sample from the subject which contains hepatitis C virus; b) contacting each serially diluted sample with a cell which is susceptible to infection by hepatitis C virus under conditions whereby the cell can be infected by hepatitis C virus in the sample; c) contacting the cell of step (b) with the cytolytic T lymphocytes of this invention under conditions whereby cytolysis of target cells can occur; d) measuring the amount of cytolysis of target cells; e) comparing the amount of cytolysis of target cells of step (d) with the amount of cytolysis of target cells by activated cytotoxic T lymphocytes contacted with cells infected with serially diluted control samples containing a known amount of hepatitis C virus; and f) determining the viral load of hepatitis C virus in the subject from the comparison of step (e).

It is also contemplated that the viral load of HCV in a subject can be determined by a) contacting HCV-infected cells (e.g., liver cells, PBMC) with the cytolytic T lymphocytes of this invention; b) measuring the amount of cytolysis of target cells or cytokine production in the CTL; c) comparing the amount of cytolysis of target cells or cytokine production in the CTL of step (b) with the amount of cytolysis of target cells or cytokine production in activated CTL contacted with cells infected with serially diluted control samples containing a known amount of hepatitis C virus; and d) determining the viral load of hepatitis C virus in the subject from the comparison of step (c).

The sample from the subject used in the methods of this invention can be any sample which can contain infectious HCV, including, but not limited to, serum, plasma, liver tissue and PBMC.

On the basis of the information provided by the above methods, a calculation of HCV viral load in a subject can be carried out according to methods standard in the art for determining viral load (88).

Finally, the present invention also provides a method of determining the prognosis of a subject diagnosed with hepatitis C virus infection, comprising determining a viral load for the subject according to the methods of this invention, whereby a high viral load can indicate a poor prognosis and a low viral load can indicate a good prognosis.

A value of HCV viral load which would be a "high" viral load of HCV and a correlation with a high viral load with a subject's prognosis can be determined according to methods well known in the art. For example, a high viral load as determined according to the methods of this invention can identify a subject who is in or likely to progress to an advanced stage of disease, as well as to provide a predictive indicator of a subject's response to treatment, such as interferon therapy (88,89,90).

For the methods of this invention wherein cytolysis of target cells is detected, detection of the cytolysis of target cells can be according to any method for detection of cytolysis of target cells now known or later developed. For example, the production of $^{51}$Cr-labeled target cells and an assay whereby cytolysis of target cells can be detected by release of $^{51}$Cr release from a target cell, are described in the Examples provided herein. Other methods for detecting cytolysis can also be used in these methods, such as release of Europium or various dyes from appropriately labeled target cells, uptake of dyes into cells or detection of apoptosis of target cells, according to methods standard in the art.

For the methods of this invention wherein the production of a cytokine in an activated cytolytic T lymphocyte is detected, the cytokine can be, but is not limited to, interleukin-2, interferon-γ, granulocyte/macrophage colony stimulating factor, interleukin-10, interleukin-4, interleukin-5 and/or interleukin-3. Detection of cytokine production can be by any method now known in the art, such as by commercially available assay or by any other method later identified for detecting the presence of a cytokine (86).

The present invention is more particularly described in the following examples which are intended as illustrative only since numerous modifications and variations therein will be apparent to those skilled in the art.

EXAMPLES

Synthetic peptides.

Peptides were prepared in an automated multiple peptide synthesizer (Symphony; Protein Technologies, Inc.) using Fmoc chemistry. Peptides were purified by reverse phase HPLC and the amino acid sequence of each of the peptides was confirmed with an Applied Biosystems 477A automated sequencer.

Cells.

The T2 cell line is deficient in TAP1 and TAP2 transporter proteins and expresses low levels of HLA-A2.1 (50,51). The human B-lymphoblastoid cell line HMYC1R was transfected with HLA-A2.1 (C1R.A2.1). Cell line C1R.AAD (HMYC1R transfected with the HLA chimeric molecule containing α1 and α2 domains from human HLA-A2.1 and α3 from mouse H-2D$^d$) has been previously described (48). Cell lines were maintained in complete T-cell medium (CTM; 1:1 mixture of RPMI:EHAA (Life Technologies; Grand Island, N.Y.) containing 10% fetal bovine serum (FBS), 4 mM glutamine, 100 U/ml penicillin, 100, µg/ml streptomycin and 50 µM 2-mercaptoethanol).

Human subjects.

Peripheral blood mononuclear cells (PBMC) were isolated from a patient with chronic HCV infection. The patient had anti HCV-specific antibodies as detected with a commercially available assay (Ortho Diagnostics, Raritan, N.J.) and was HCV RNA positive by PCR.

Mice.

Transgenic A2Kb mice (Scripps Research Inst.) and transgenic AAD mice (University of Virginia) were bred in the colony at BioCon Inc. (Rockville, Md.). These animals have been previously described (48,52) and they express α1 and α2 domains from human HLA-A2.1 molecule and α3 domain from mouse H-2K$^b$ and H-2D$^d$ molecules, respectively.

Binding Assays.

Peptide binding to HLA molecules was measured using the T2 mutant cell line according to a protocol previously described (53). T2 cells (3×10$^5$/well) were incubated overnight in 96-well plates with culture medium (1:1 mixture of RPMI 1640: EHAA containing 2.5% FBS, 100 U/ml penicillin, 100 μg/ml streptomycin) with 10 μg/ml β2-microglobulin (Sigma Chemical Co; St. Louis, Mo.) and different peptide concentrations. The next day, cells were washed twice with cold PBS containing 2% FBS and incubated for 30 min at 4° C. with anti HLA-A2.1 BB7.2 monoclonal antibody (1/80 dilution from hybridoma supernatant) and 5 μg/ml FITC-labeled goat anti mouse Ig (Pharmingen; San Diego, Calif.). Cells were washed twice after each incubation and HLA-A2.1 expression was measured by flow cytometry on a FACScan (Becton Dickinson). HLA-A2.1 expression was quantified as fluorescence index (FI) according to the formula: FI=(mean fluorescence with peptide—mean fluorescence without peptide)/mean fluorescence without peptide. Background fluorescence without BB7.2 antibody was subtracted for each individual value. In order to compare the different peptides, FI$_{0.5}$, the peptide concentration that increases HLA-A2.1 expression by 50% over no peptide control background, was calculated from the titration curve for each peptide.

Generation of human CTL.

Cytotoxic T lymphocytes (CTL) lines were generated according to the protocol previously described (12,14). PBMC from a patient chronically infected with HCV were separated by Ficoll-Hypaque and 10$^6$ cells were stimulated in 400 μl CTM in 48-well plates with 2×10$^6$ autologous cells pulsed previously for 3 h with 10 μM peptide in CTM. After 3 days, the same volume of CTM with IL-2 (10% vol./vol.) was added to each well and the cells were further expanded on day six with CTM containing IL-2. This cycle was repeated every ten days. For the first three cycles, 2×10$^6$ peptide-pulsed, irradiated (3000 rads) autologous PBMC were used as antigen presenting cells (APC) and in subsequent cycles, CTL were stimulated with 3×10$^5$ peptide-pulsed, irradiated (3000 rads) autologous Con A blasts and 1.5×10$^6$ irradiated allogeneic PBMC. Con A blasts were obtained by stimulating PBMC with 10 μg/ml Concanavalin A and expanding with CTM containing 50 U/ml IL-2 and 1 U/ml IL-6. Con A blasts were stimulated with Con A every 8–10 days. The stimulation of PBMC with peptide results in the expansion of peptide antigen-specific CTL, while non-specific cells that are not stimulated die out, resulting in a CTL line that is specific for the peptide. This enrichment, resulting in an essentially homogeneous population of peptide antigen-specific CTL occurs after about 3–5 cycles of stimulation. Using this procedure, a CTL line, ViT2, was raised from a patient with chronic, active HCV infection.

Generation of mouse CTL.

Eight to twelve week old mice were immunized subcutaneously (s.c.) in the base of the tail with 100 μl of an emulsion containing 1:1 incomplete Freund's adjuvant (IFA) and PBS solution with peptides (antigens) and cytokines (50 nmol CTL epitope, 50 nmol HBV core (aa) 128–140 helper epitope, 3 μg IL-12 and 3 μg GM-CSF) (54). Mice were boosted 2 weeks later and spleens removed 10–14 days after the boost. Immune spleen cells (2.5×10$^6$/well) were stimulated in 24-well plates with autologous spleen cells (5×10$^6$/well) pulsed for 2 h with 10 μM CTL epitope peptide in CTM with 10% T-STIM (Collaborative Biomedical Products, Bedford, Mass.). After further in vitro stimulation with peptide-pulsed, syngeneic spleen cells, CTL lines were produced and maintained by weekly restimulation of 10$^6$ CTL/well with 2×10$^5$ peptide-pulsed, irradiated (10,000 rads) C1R.AAD cells and 4×10$^6$ C57/B16 irradiated (3000 rads) spleen cells as feeders.

Cytotoxicity assay.

CTL activity was measured using a 4 h assay with $^{51}$Cr-labeled target cells. Target cells (10$^6$) were pulsed in 100 μl CTM with or without 10 μM peptide and 150 μCi $^{51}$Cr for 2 h, washed three times and added to the plates containing different amounts of CTL (effector) cells in a final volume of 200 μl CTM. In peptide titration assays, target cells were pulsed with $^{51}$Cr for 2 h, washed three times and added to the plates with different peptide concentrations. Effector cells were added 2 h later and the supernatants were harvested and counted after an additional 4 h incubation. The percentage of specific $^{51}$Cr release was calculated as: 100×(experimental release—spontaneous release)/(maximum release—spontaneous release). Spontaneous release was determined from target cells incubated without effector cells and maximum release was determined in the presence of 5% Triton X-100. C1R.A2.1 and C1R.AAD lines and AAD and A2Kb Con A blasts were used as target cells. Con A blasts were prepared by culturing 3×10$^6$ spleen cells in 2 ml of CTM in the presence of 2 μg/ml of Con A in 24-well culture plates. After 2 days, cells were harvested and processed for labeling as described.

C7A2 Ala-substituted peptides binding to HLA-A2.1 molecules.

The binding affinity of wild-type C7A2 peptide (C7A2-WT) was evaluated with a T2 binding assay (53), which measures the cell surface stabilization of HLA-A2.1 molecules after incubation with peptide. In order to compare the different peptides, a fluorescence index value of 0.5 (FI$_{0.5}$), the peptide concentration that increases HLA-A2.1 expression by 50%, was chosen as a way to compare titrations of the peptides and relative affinity for MHC molecules. Using this method, FI$_{0.5}$ of 10 μM was calculated for C7A2-WT.

In a first set of experiments to define key functional residues, peptides with alanine substitutions at each one of the positions were synthesized and tested in binding assays (Table I). C7A2-WT has the typical motif for binding to HLA-A2.1, with L and V at positions 2 and 9 respectively (22,23). Binding experiments with these alanine-substituted peptides showed (FIG. 1A) that peptide 2A had lost binding ability, in accordance with the anchor character of this position, and also 9A had impaired binding, although not as much as 2A, since Ala can function as a weak anchor at position 9. Other substitutions that decreased binding were 6A and 7A, indicating the importance of these residues as secondary anchor positions. Peptides 4A and 8A had higher affinity, with FI$_{0.5}$ around 2 μM. Substitutions at positions 1, 3 and 5 had no effect on peptide binding.

Binding of peptides with substitutions at position 1.

C7A2-WT has aspartic acid, a negatively charged residue, in position 1 (28). Substitution by Ala at this position, although replacing the charged residue, did not improve binding, so the original D was replaced by other residues. Peptides with aromatic amino acids at this position (F and H), as well as N (which eliminates the negative charge but keeps the size), or S and T, small polar amino acids which can form hydrogen bonds, were synthesized.

Peptides 1N, 1H and 1T had improved binding affinity, whereas 1F had a $FI_{0.5}$ higher than C7A2-WT, indicating lower affinity. Solubility problems with 1F may account for impaired binding ability in this case.

Binding of peptides with substitutions at other positions.

Substitution by A at position 7 yielded a peptide with impaired binding ability. The natural amino acid at this position is P, which is known to induce turns in peptide chains. In order to determine whether the A replacement changed the structure of the peptide chain or eliminated the side chain responsible for interaction with HLA-A2.1, 7G was synthesized, thereby introducing an amino acid that also contributes to β turns as does P, but lacks the side chain. 7V was also synthesized, with an aliphatic side chain bulkier than A. None of these peptides bound to HLA-A2.1 (FIG. 1B), demonstrating a specific role of the P side chain in the binding to HLA-A2.1.

Position 3 was replaced by W and by K, L, I and V, which are charged and aliphatic residues. Binding was improved with 3W (FIG. 1B), but it was completely abolished in 3K. Peptide 3V had impaired binding, whereas 3L and 3I were similar to C7A2-WT.

Replacement of position 8L with a V introduced an aliphatic residue similar to A and L (amino acid present in C7A2-WT), but with an intermediate size between them. Peptide 8V is one of the few sequence variations that can be found within this epitope and is common in viral isolates belonging to HCV genotypes 2a and 2b (56,57). Peptide 8V had an $FI_{0.5}$ of 15 μM, which was in the range of C7A2-WT.

Recognition of C7A2-variant peptides by human CTL.

To identify residues involved in CTL recognition, a CTL line specific for C7A2 was established as described herein from PBMC from an HCV infected patient after several rounds of C7A2-WT peptide stimulation. Lytic activity of these CTL was tested with target cells incubated with different concentrations of each peptides to study the recognition of the different peptide variants and titrate T-cell avidity. The Ala-substituted peptides, 2A and 9A were not recognized (FIG. 2A), in accordance with the anchor character of these positions. Also, 3A was not recognized, despite good HLA-A2.1 binding, indicating the epitopic character of this position. Peptides 4A, 5A, 6A and 7A, although recognized at the highest concentrations, showed poorer recognition than C7A2-WT, as a consequence in some cases, of poorer MHC binding (6A and 7A), or otherwise of impaired T-cell recognition (4A and 5A). Peptides 1A and 8A showed higher levels of ysis than C7A2-WT and titrated at 10-fold lower concentrations.

Of the non-Ala substituted peptides (FIG. 2B), none was recognized by the CTL at the concentrations tested (including those having high binding affinity, such as 1N or 1T), with the exception of 8V, which behaved similarly to C7A2-WT, and 1H, that induced marginal lysis at the highest concentration tested.

Recognition of C7A2-variant peptides by HLA-A2.1 transgenic mice CTL.

AAD transgenic mice express α1 and α2 domains from the human HLA-A2.1 molecule and α3 domain from the mouse $D^d$ molecule (48). Transgenic mice expressing human HLA-A2.1 molecules have been described as a model of presentation and recognition of several HLA-A2.1-restricted antigens (9,37,47,58–60) and allow testing of immunogenicity in the context of a human HLA molecule prior to immunizing humans. In order to use the peptide antigens in this model, recognition of the different C7A2 peptide variants by murine CTL in vitro was studied prior to testing the immunogenicity of the different peptides in vivo.

CTL lines AAD.10 and AAD.1 were induced by immunization with peptide C7A2-WT together with a helper epitope presented by the $H-2^b$ class II MHC molecules of this mouse strain and GM-CSF and IL-12 according to the method of Ahlers et al. (54) and as described herein. After ten to twelve in vitro stimulations with C7A2-WT, these cell lines were tested against the whole panel of C7A2-substituted peptides in a lytic assay to compare the recognition of the different peptides with that by the human CTL line.

Of the Ala-substituted peptides (FIGS. 3A and 3C), 1A and 8A were able to sensitize target cells in a concentration range around that of C7A2-WT, 1A being more effective than 8A for both lines. The other peptides titrated at several 10-fold concentrations higher. Peptides 5A, 7A and 2A required the highest concentrations to induce significant lysis, whereas 3A, 6A, 4A and 9A titrated at intermediate concentrations. Position 5 was clearly shown to be an epitopic residue and almost no significant lysis was obtained with target cells sensitized with peptide 5A, as it had been observed for position 3 in the human CTL line. Peptide 3A titrated at a lower concentration, suggesting that in the case of the murine HLA-A2.1-restricted CTL lines, position 3 is not involved in TCR binding as clearly as in the human line. Finally, peptides with substitutions at positions 4 and 6 were recognized as in the case of the human CTL line.

Peptides with substitutions by other amino acids and positive binding to HLA-A2.1 were also tested for recognition by AAD mouse CTL lines (FIGS. 3B and 3D). These peptides contained mainly substitutions at position 1, except for peptides 8V and 3W. Surprisingly, with the exception of 1S, that required a high peptide concentration to sensitize target cells, all the peptides with substitutions at position 1 were recognized by AAD mouse CTL lines in a concentration range similar to that observed for C7A2-WT and some peptides, such as 1F, induced a higher response with line. AAD.10. Peptide 8V was recognized at higher concentrations than determined for C7A2-WT, whereas peptide 3W was not recognized at any of the concentrations tested.

In vivo inmmunogenicity of C7A2-derived peptides in HLA-A2.1 transgenic mice.

After studying the recognition of C7A2-derived peptides by human and AAD transgenic murine CTL, the in vivo immunogenicity of these peptides was studied in the AAD transgenic mouse model. Different groups of animals were immunized with the substituted CTL peptides (epitopes) in conjunction with a helper epitope and cytokines as described above and the ability to induce an immune response was tested in CTL cytotoxicity assays. Included in these assays were some of the peptides with positive binding that were recognized by AAD mouse CTL lines. As shown in FIG. 4, peptides C7A2-WT and 8A were able to induce clear CTL responses, whereas 1A could induce only a marginal response. In contrast, peptides 1N and 1F were unable to induce any measurable CTL response.

Induction of CTL immune response against C7A2-WT by C7A2-WT and 8A peptides in HLA-A2.1 transgenic mice.

Among all the peptides tested in binding assays to HLA-A2.1 and for recognition by human and transgenic mice CTL, peptide 8A was the most promising. This peptide was able to bind at lower concentrations than C7A2-WT, sensitized human and mouse target cells in the same range or even at lower concentrations than C7A2-WT and in immunization experiments, induced higher levels of lysis. Therefore, the ability of 8A to induce a CTL immune response against C7A2-WT was tested in the next set of experiments.

Each peptide was used to immunize two groups of animals, with 50 or 15 nmol CTL epitope peptide as described herein. After two immunizations, spleen cells were removed and stimulated in vitro with the same peptide used for immunization and lytic activity against C7A2-WT (and 8A in the groups immunized with 8A) was tested. As shown in FIG. 5, two of the four animals immunized with C7A2-WT were able to respond to this peptide. In the animals immunized with 8A, strong responses to C7A2-WT could be detected, together with positive responses to 8A itself, even in the group of mice immunized with 15 nmol peptide (FIG. 5B).

In a second group of experiments, A2Kb transgenic mice, that express a chimeric HLA molecule with α1 and α2 domains from human HLA-A2.1 and α3 domain from mouse $K^b$, were immunized with 50 nmol C7A2-WT or 8A peptide and the ability of these peptides to induce a CTL immune response recognizing C7A2-WT was tested. FIG. 6 shows that, as seen with the AAD mice, C7A2-WT induced a low response, whereas the immunization with 8A induced a higher level of response by CTL that recognized both C7A2-WT and 8A, even with a lower E/T ratio in the CTL assay (70:1 vs. 120:1).

CTL avidity for a target peptide-MHC complex, defined as the sensitivity to detect low densities of peptide-MHC complex on the surface of target or stimulator cells, has been shown to make a substantial difference in the ability of CTL to clear a virus infection in vivo, in two murine model systems (61,62). Therefore, to determine whether the CTL raised against the modified peptide 8A were of as high avidity against targets presenting the wild-type peptide as would be CTL raised against the wild-type peptide itself, C7A2-WT was titrated on target cells and the (lysis) killing by short term CTL lines (which received 3–4 cycles of in vitro stimulation with peptide) raised against this peptide or against 8A was compared (FIG. 7). The CTL raised against 8A killed targets expressing the C7A2-WT at concentrations more than 100-fold lower than were required to get comparable levels of killing by the CTL raised against the C7A2-WT itself Thus, use of the modified peptide in this case increases not only immunogenicity, but also the avidity of the CTL that are produced, an additional advantage for the potential efficacy of a vaccine.

Recognition of peptide 8V by CTL from HLA-A2.1 transgenic mice immunized with 8A.

As mentioned above, one of the peptides recognized by both human and mouse C7A2-WT specific CTL lines is peptide 8V. This peptide is common in viral isolates from HCV genotypes 2a and 2b (56,57). Since 8A has a change in the same position, it was an interesting point to know if CTL induced by immunization with 8A were cross reactive not only with C7A2-WT, which corresponds to viral sequences from genotypes 1a, 1b and 3a, but also with peptide 8V, belonging to viral sequences from genotype 2. Results in FIGS. 8A and 8B show that CTL induced by immunization with 8A recognize peptide 8V both in AAD mice (FIG. 8A) and in A2Kb mice (FIG. 8B) in a manner similar to the recognition of C7A2-WT.

Enhanced epitope C7A2-8A in DNA vaccine against HCV.

To produce a DNA vaccine encoding the enhanced epitope of this invention, a DNA plasmid vaccine expressing HCV core protein was first prepared. The vector AC7, encoding the entire nucleocapsid (core) region of HCV H (1a) strain (91) (amino acids 1–191) was constructed. The sequence was amplified by polymerase chain reaction (PCR) and inserted into the Hind III and Bam HI sites of the eukaryotic expression vector pWRG7020 under the transcriptional control of the cytomegalovirus early promoter. (Agracetus Inc., Middleton, Wis.). Direct sequencing of the insert DNA using the fluorescent dye terminator cycle method on an ABI 310 automated sequencer (Applied Biosystems, Forester City, Calif.) showed the expected sequence in frame. Plasmid AC7 was amplified in *Escherichia coli,* purified using Quiagen purification kit (Quiagen Inc., Chatsworth, Calif.), and maintained at −20° C. until use.

Transient expression of HCV core protein in cell culture was confirmed in human 293 cells, as previously described (92). Briefly, the plasmid was transfected into 293 cells using lipofectamine (GIBCO/BRL) and protein expression was analyzed by indirect immunofluorescence staining and immunoblotting using a specific mouse monoclonal antibody recognizing HCV core (6G7; Stanford University, Palo Alto Va. Medical Center, Palo Alto, Calif.; ref 93). For immunization, AC7 was precipitated with 3M sodium acetate and ethanol and redissolved in phosphate buffered saline (PBS).

A variant of this plasmid was then constructed with the substitution of an Ala codon for a Leu codon at amino acid residue position 8 of the epitope C7A2. The codon at nucleotides 756–758 in the core of the HCV genome region was changed from CTC (Leu) to GCG (Ala) by PCR amplification. Forward (8AF: TCATGGGGTACATACCG-GCGGTC nt. 739–761) (SEQ ID NO:5) and reverse (8AR: TCCAAGAGGGGCGCCGACCGCCG nt. 776–754) (SEQ ID NO:6) primers were synthesized containing the 8A sequence at this location. Two overlapping PCR products were generated using primers 243F (AAGACTGCTAGCCGAGTAGTG nt.243–263) (SEQ ID NO:7) and 8AR or 8AF and 980R (CACAATACTCGAGTTAGGGC nt.980–961) (SEQ ID NO:8). Following gel isolation of the PCR products, an assembly PCR was carried out using 100 ng of each of the fragments and primers to generate the full length core sequence with Hind III and Not I restriction sites engineered at the 5' and 3' ends, respectively. This product was cloned into the vector WRG7020 and the sequence verified by the fluorescent dye terminator cycle method as described above.

AAD mice, transgenic for the human HLA molecule HLA-A2.1 with the alpha-3 domain from H-$2D^d$ were immunized i.m. in the quadriceps major on days 0, 14, and 28 with 100, 30, or 10 μg doses of AC7 or AC7-8A, or 100 μg pWRG7020 (plasmid without the HCV core gene insert, as control mock vaccine) dissolved in PBS solution. Four weeks after the last immunization, spleen cells from AC7-immunized mice were stimulated in vitro with C7A2 peptide and those from AC7-8A-immunized mice were stimulated in vitro with C7A2-8A peptide, and all were assayed for CTL activity against C1R-AAD targets coated with the C7A2 peptide. The C1R-AAD cells express only the chimeric HLA-A2.1 class I molecule and no class II MHC molecules, so the CTL activity was restricted to class I HLA-A2.1. As shown in FIG. 9, at the 30 μg dose, all three mice immunized with the AC7-8A DNA vaccine had substantially higher CTL activity than the three mice imnmunized with the unmodified AC7 DNA vaccine. The same effect was seen at the 100 and 10 μg doses, but the magnitude of the difference was less.

To test efficacy for clearing a viral infection, AAD mice, transgenic for the human HLA-A2.1 molecule with the alpha-3 domain of H-2D$^d$ to be compatible with murine CD8, were infected with a recombinant vaccinia virus expressing the entire HCV core protein. This core protein gene did not contain the 8A modification, but rather was representative of the wild-type HCV. The vaccinia virus preferentially replicates in the ovaries and the titer of vaccinia in the ovaries (pfu/ovary) was used as a measure of the ability of the vaccine to reduce the level of viral infection. Mice were immunized on days 0, 14, and 28, as above, and two weeks after the last immunization, the mice were challenged intraperitoneally with 1×10$^7$ pfu of rVV-core (recombinant vaccinia virus expressing HCV core). Mice were sacrificed for harvest of ovaries 5 days after challenge. Some mice were treated 7, 6, 5, and 4 days before sacrifice with 0.5 mg anti-CD8 antibody intraperitoneally in order to determine the dependence of protection on CD8$^{30}$ cells. The ovaries (where this vaccinia virus preferentially replicates; 61,95) were harvested, homogenized, sonicated, and assayed for rVV-core titer by plating 10-fold dilutions on BSC-1 indicator cells, and staining with 0.075 w/v % crystal violet. The minimal detectable level of virus was 100 pfu/ovary. Three mice were used in each group.

As shown in Table I, at the optimal 30 μg dose of vaccine, AC7 unmodified core vaccine reduced the titers not quite 5 logs, compared to the control mice immunized with mock vaccine (mice #1–3, with titers of 3–4×10$^3$, compared to mice #13–15, with titers of 1.6–2.8×10$^8$). However, mice #7–9, immunized with the modified DNA vaccine AC7-8A, had titers reduced to undetectable levels. With both DNA vaccines, treatment of the mice with anti-CD8 antibody completely abrogated protection (mice #4–6 and #10–12), indicating that the protection was completely dependent on CD8$^+$ cells (CTL). Thus, the modified HCV-core DNA vaccine with the 8A-modified epitope is more effective than the wild-type HCV-core DNA vaccine in inducing CD8$^+$ CTL restricted to the human HLA-A2 molecule and in inducing CD8$^+$ protection against a surrogate virus expressing the HCV core protein. Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

References

1. Choo, Q.-L., G. Kuo, A. J. Weiner, L. R. Overby, D. W. Bradley, and M. Houghton. 1989. Isolation of a cDNA clone derived from blood-borne non-A, non-B viral hepatitis genome. *Science* 244:359–362.
2. Dienstag, J. L. 1983. Non-A, non-B hepatitis. I. recognition, epidemiology, and clinical features. *Gastroenterology* 85:439–462.
3. Townsend, A. and H. Bodmer. 1989. Antigen recognition by class I-restricted T lymphocytes. *Annu. Rev. Immmunol.* 7:601–624.
4. Kast, W. M., R. Offringa, P. J. Peters, A. C. Voordouw, R. H. Meloen, A. J. van der Eb, and C. J. M. Melief. 1989. Eradication of adenovirus E1-induced tumors by E1A-specific cytotoxic T lymphocytes. *Cell* 59:603–614.
5. Kast, W. M., L. Roux, J. Curren, H. J. J. Blom, A. C. Voordouw, R. H. Meloen, D. Kolakofsky, and C. J. M. Melief. 1991. Protection against lethal Sendai virus infection by in vivo priming of virus-specific cytotoxic T lymphocytes with a free synthetic peptide. *Proc. Natl. Acad. Sci. USA* 88:2283–2287.
6. Schulz, M., R. M. Zinkernagel, and H. Hengartner. 1991. Peptide-induced antiviral protection by cytotoxic T cells. *Proc. Natl. Acad. Sci. USA* 88:991–993.
7. Taylor, P. M. and B. A. Askonas. 1986. Influenza nucleoprotein-specific cytotoxic T-cell clones are protective in vivo. *Immunology* 58:417–420.
8. Shirai, M., H. Okada, M. Nishioka, T. Akatsuka, C. Wychowski, R. Houghten, C. D. Pendleton, S. M. Feinstone, and J. A. Berzofsky. 1994. An epitope in hepatitis C virus core region recognized by cytotoxic T cells in mice and humans. *J. Virol.* 68:3334–3342.
9. Shirai, M., T. Arichi, M. Nishioka, T. Nomura, K. Ikeda, K. Kawanishi, V. H. Engelhard, S. M. Feinstone, and J. A. Berzofsky. 1995. CTL responses of HLA-A2.1-transgenic mice specific for hepatitis C viral peptides predict epitopes for CTL of humans carrying HLA-A2.1 *J. Immunol.* 154:2733–2742.
10. Cerny, A., J. G. McHutchison, C. Pasquinelli, M. E. Brown, M. A. Brothers, B. Grabscheid, P. Fowler, M. Houghton, and F. V. Chisari. 1995. Cytotoxic T lymphocyte response to hepatitis C virus-derived peptides containing the HLA A2.1 binding motif. *J Clin. Invest.* 95:521–530.
11. Koziel, M. J., D. Dudley, N. Afdhal, Q.-L. Choo, M. Houghton, R. Ralston, and B. D. Walker. 1993. Hepatitis C virus (HCV)-specific cytotoxic T lymphocytes recognize epitopes in the core and envelope proteins of HCV. *J. Virol.* 67:7522–7532.
12. Battegay, M., J. Fikes, A. M. Di Bisceglie, P. A. Wentworth, A. Sette, E. Celis, W. -M. Ching, A. Grakoui, C. M. Rice, K. Kurokohchi, J. A. Berzofsky, J. H. Hoofnagle, S. M. Feinstone, and T. Akatsuka. 1995. Patients with chronic hepatitis C have circulating cytotoxic T cells which recognize hepatitis C virus C-encoded peptides binding to HLA-A2.1 molecules. *J. Virol.* 69:2462–2470.
13. Kita, H., T. Moriyama, T. Kaneko, I. Harase, M. Nomura, H. Miura, I. Nakamura, Y. Yazaki, and M. Imawari. 1993. HLA B44-restricted cytotoxic T lymphocytes recognizing an epitope on hepatitis C virus nucleocapsid protein. *Hepatology* 18:1039–1044.
14. Kurokohchi, K., T. Akatsuka, C. D. Pendleton, A. Takamizawa, M. Nishioka, M. Battegay, S. M. Feinstone, and J. A. Berzofsky. 1996. Use of recombinant protein to identify a motif-negative human CTL epitope presented by HLA-A2 in the hepatitis C virus NS3 region. *J. Virol* 70:232–240.
15. Koziel, M. J., D. Dudley, J. T. Wong, J. Dienstag, M. Houghton, R. Ralston, and B. D. Walker. 1992. Intrahepatic cytotoxic T lymphocytes specific for hepatitis C virus in persons with chronic hepatitis. *J. Immunol.* 149:3339–3344.
16. Erickson, A. L., M. Houghton, Q.-L. Choo, A. J. Weiner, R. Ralston, E. Muchmore, and C. M. Walker. 1993. Hepatitis C virus-specific responses in the liver of chimpanzees with acute and chronic hepatitis C. *J Immunol.* 151:4189–4199.
17. Rehermann, B., K. M. Chang, J. G. McHutchison, R. Kokka, M. Houghton, and F. V. Chisari. 1996. Quantitative analysis of the peripheral blood cytotoxic T lymphocyte response in patients with chronic hepatitis C virus infection. *J. Clin. Invest.* 98:1432–1440.
18. Chisari, F. V. 1997. Cytotoxic T cells and viral hepatitis. *J. Clin. Invest.* 99:1472–1477.
19. Townsend, A. R. M., J. Rothbard, F. M. Gotch, G. Bahadur, D. Wraith, and A. J. McMichael. 1986. The epitopes of influenza nucleoprotein recognized by cytotoxic T lymphocytes can be defined with short synthetic peptides. *Cell* 44:959–968.

20. Germain, R. N. and D. H. Margulies. 1993. The biochemistry and cell biology of antigen processing and presentation. *Annu. Rev. Immunol.* 11:403–450.
21. Matsumura, M., D. H. Fremont, P. A. Peterson, and I. A. Wilson. 1992. Emerging principles for the recognition of peptide antigens by MHC class I molecules. *Science* 257:927–934.
22. Falk, K., O. Rötzschke, S. Stevanovic, G. Jung, and H.-G. Rammensee. 1991. Allele-specific motifs revealed by sequencing of self-peptides eluted from MHC molecules. *Nature* 351:290–296.
23. Hunt, D. F., R. A. Henderson, J. Shabanowitz, K. Sakaguchi, H. Michel, N. Sevilir, A. L. Cox, E. Appella, and V. H. Engelhard. 1992. Characterization of peptides bound to the class I MHC molecule HLA-A2.1 by mass spectrometry. *Science* 255:1261–1263.
24. Kast, W. M., R. M. P. Brandt, J. Sidney, J.-W. Drijfhout, R. T. Kubo, H. M. Grey, C. J. M. Melief, and A. Sette. 1994. Role of HLA-A motifs in identification of potential CTL epitopes in human papillomavirus type 16 E6 and E7 proteins. *J. Immunol.* 152:3904–3912.
25. Sidney, J., H. M. Grey, S. Southwood, E. Celis, P. A. Wentworth, M.-F. del Guercio, R. T. Kubo, R. W. Chestnut, and A. Sette. 1996. Definition of an HLA-A3-like supermotif demonstrates the overlapping peptide-binding repertoires of common HLA molecules. *Hum. Immunol.* 45:79–93.
26. Rötzschke, O. and K. Falk. 1991. Naturally-occurring peptide antigens derived from the MHC class-I-restricted processing pathway. *Immunol. Today* 12:447–455.
27. Parker, K. C., M. A. Bednarek, L. K. Hull, U. Utz, B. Cunningham, H. J. Zweerink, W. E. Biddison, and J. E. Coligan. 1992. Sequence motifs important for peptide binding to the human MHC class I molecule, HLA-A2. *J. Immunol.* 149:3580–3587.
28. Ruppert, J., J. Sidney, E. Celis, R. T. Kubo, H. M. Grey, and A. Sette. 1993. Prominent role of secondary anchor residues in peptide binding to HLA-A2.1 molecules. *Cell* 74:929–937.
29. Parker, D. C., M. A. Bednarek, and J. E. Coligan. 1994. Scheme for ranking potential HLA-A2 binding peptides based on independent binding of individual peptide side-chains. *J. Immunol.* 152:163–175.
30. Wentworth, P. A., A. Sette, E. Celis, J. Sidney, S. Southwood, C. Crimi, S. Stitely, E. Keogh, N. C. Wong, B. Livingston, D. Alazard, A. Vitiello, H. M. Grey, F. V. Chisari, R. W. Chesnut, and J. Fikes. 1996. Identification of A2-restricted hepatitis C virus-specific cytotoxic T lymphocyte epitopes from conserved regions of the viral genome. *Internat. Immunol.* 8:651–659.
31. Gulukota, K. and C. DeLisi. 1996. HLA allele selection for designing peptide vaccines. *Genet Anal* 13:81–86.
32. Lipford, G. B., S. Bauer, H. Wagner, and K. Heeg. 1995. Peptide engineering allows cytotoxic T-cell vaccination against human papilloma virus tumour antigen, E6. *Immunology* 84:298–303.
33. Lipford, G. B., S. Bauer, H. Wagner, and K. Heeg. 1995. In vivo CTL induction with point-substituted ovalbumin peptides: immunogenicity correlates with peptide-induced MHC class I stability. *Vaccine* 13:313–320.
34. Pogue, R. R., J. Eron, J. A. Frelinger, and M. Matsui. 1995. Amino-terminal alteration of the HLA-A*0201-restricted human immunodeficiency virus pol peptide increases complex stability and in vitro immunogenicity. *Proc. Natl. Acad. Sci. U.S.A.* 92:8166–8170.
35. Parkhurst, M. R., M. L. Salgaller, S. Southwood, P. F. Robbins, A. Sette, S. A. Rosenberg, and Y. Kawakami. 1996. Improved induction of melanoma-reactive CTL with peptides from the melanoma antigen gp 100 modified at HLA-A*0201-binding residues. *J. Immunol.* 157:2539–2548.
36. Sette, A., A. Vitiello, B. Reherman, P. Fowler, R. Nayersina, W. M. Kast, C. J. M. Melief, C. Oseroff, L. Yuan, J. Ruppert, J. Sidney, M.-F. del Guercio, S. Southwood, R. T. Kubo, R. W. Chesnut, H. M. Grey, and F. V. Chisari. 1994. The relationship between class I binding affinity and immunogenicity of potential cytotoxic T cell epitopes. *J. Immunol.* 153:5586–5592.
37. Wentworth, P. A., A. Vitiello, J. Sidney, E. Keogh, R. W. Chesnut, H. Grey, and A. Sette. 1996. Differences and similarities in the A2.1-restricted cytotoxic T cell repertoire in humans and human leukocyte and antigen-transgenic mice. *Eur. J. Immunol.* 26:97–101.
38. Boehncke, W.-H., T. Takeshita, C. D. Pendleton, S. Sadegh-Nasseri, L. Racioppi, R. A. Houghten, J. A. Berzofsky, and R. N. Germain. 1993. The importance of dominant negative effects of amino acids side chain substitution in peptide-MHC molecule interactions and T cell recognition. *J. Immunol.* 150:331–341.
39. Altuvia, Y., J. A. Berzofsky, R. Rosenfeld, and H. Margalit. 1994. Sequence features that correlate with MHC restriction. *Molec. Immunol.* 31:1–19.
40. Mueller, D. L., M. K. Jenkins, and R. H. Schwartz. 1989. Clonal expansion versus functional clonal inactivation: A costimulatory signaling pathway determines the outcome of T cell antigen receptor occupancy. *Annu. Rev. Immunol.* 7:445–480.
41. Weaver, C. T. and E. R. Unanue. 1990. The costimulatory function of antigen-presenting cells. *Immunol. Today.* 11:49–55.
47. Vitiello, A., D. Marchesini, J. Furze, L. A. Sherman, and R. W. Chesnut. 1991. Analysis of the HLA-restricted influenza-specific cytotoxic T lymphocyte response in transgenic mice carrying a chimeric human-mouse class I major histocompatibility complex. *J. Exp. Med.* 173:1007–1015.
48. Newberg, M. H., D. H. Smith, D. R. Vining, E. Lacy, and V. H. Engelhard. 1996. Importance of MHC class I α2 and α3 domains in the recognition of self and non-self MHC molecules. *J. Immunol.* 156:2473–2480.
50. Salter, R. D., D. N. Howell, and P. Cresswell. 1985. Genes regulating HLA class I antigen expression in T-B lymphoblast hybrids. *Immunogenetics* 21:235–246.
51. Spies, T. and R. DeMars. 1991. Restored expression of major histocompatibility class I molecules by gene transfer of a putative peptide transporter. *Nature* 351:323–324.
52. Irwin, M. J., W. R. Heath, and L. A. Sherman. 1989. Species-restricted interactions between CD8 and the α3 domain of class I influence the magnitude of the xenogeneic response. *J. Exp. Med.* 170:1091–1101.
53. Nijman, H. W., J. G. A. Houbiers, M. P. M. Vierboom, S. H. van der Burg, J. W. Drijfhout, J. D'Amaro, P. Kenemans, C. J. M. Melief, and W. M. Kast. 1993. Identification of peptide sequences that potentially trigger HLA-A2.1-restricted cytotoxic T lymphocytes. *Eur. J. Immunol.* 23:1215–1219.
54. Ahlers, J. D., N. Dunlop, D. W. Alling, P. L. Nara, and J. A. Berzofsky. 1997. Cytokine-in-adjuvant steering of the immune response phenotype to HIV-1 vaccine constructs: GM-CSF and TNFα synergize with IL-12 to enhance induction of CTL. *J. Immunol.* 158:3947–3958.
56. Okamoto, H., S. Okada, Y. Sugiyama, K. Kurai, H. Iizuka, A. Machida, Y. Miyakawa, and M. Mayumi. 1991. Nucleotide sequence of the genomic RNA of hepatitis C virus isolated from a human carrier: comparison with reported isolates for conserved and divergent regions. *J. Gen. Virol.* 72:2697–2704.
57. Okamoto, H., K. Kurai, S.-I. Okada, K. Yamamoto, H. Iizuka, T. Tanaka, S. Fukuda, F. Tsuda, and S. Mishiro. 1992. Full-length sequence of a hepatitis C virus genome having poor homology to reported isolates: comparative study of four distinct genotypes. *Virology* 188:331–341.

58. Ressing, M. E., A. Sette, R. M. P. Brandt, J. Ruppert, P. A. Wentworth, M. Hartman, C. Oseroff, H. M. Grey, C. J. M. Melief, and W. M. Kast. 1995. Human CTL epitopes encoded by human papillomavirus type 16 E6 and E7 identified through in vivo and in vitro immunogenicity studies of HLA-A*0201-binding peptides. *J. Immunol.* 154:5934–5943.
59. Engelhard, V. H., E. Lacy, and J. P. Ridge. 1991. Influenza A-specific, HLA-A2.1-restricted cytotoxic T lymphocytes from HLA-A2.1 transgenic mice recognize fragments of the M1 protein. *J. Immunol.* 146:1226–1232.
60. Newberg, M. H., J. P. Ridge, D. R. Vining, R. D. Salter, and V. H. Engelhard. 1992. Species specificity in the interaction of CD8 with the a3 domain of MHC class I molecules. *J. Immunol.* 149:136–142.
61. Alexander-Miller, M. A., G. R. Leggatt, and J. A. Berzofsky. 1996. Selective expansion of high or low avidity cytotoxic T lymphocytes and efficacy for adoptive immunotherapy. *Proc. Natl. Acad. Sci. U.S.A.* 93:4102–4107.
62. Gallimore, A., T. Dumrese, H. Hengartner, R. M. Zinkernagel, and H. G. Rammensee. 1998. Protective immunity does not correlate with the hierarchy of virus-specific cytotoxic T cell responses to naturally processed peptides. *J Exp Med.* 187:1647–1657.
70. Pastan et al. "A retrovirus carrying an MDR1 cDNA confers multidrug resistance and polarized expression of P-glycoprotein in MDCK cells." *Proc. Nat. Acad. Sci.* 85:4486 (1988)
71. Miller et al. "Redesign of retrovirus packaging cell lines to avoid recombination leading to helper virus production." *Mol. Cell Biol.* 6:2895 (1986)).
72. Mitani et al. "Transduction of human bone marrow by adenoviral vector." *Human Gene Therapy* 5:941–948 (1994)).
73. Goodman et al. "Recombinant adeno-associated virus-mediated gene transfer into hematopoietic progenitor cells." *Blood* 84:1492–1500 (1994))
74. Naidini et al. "In vivo gene delivery and stable transduction of nondividing cells by a lentiviral vector." *Science* 272:263–267 (1996))
75. Agrawal et al. "Cell-cycle kinetics and VSV-G pseudotyped retrovirus mediated gene transfer in blood-derived CD34+ cells." *Exp. Hematol.* 24:738–747 (1996)).
76. Schwarzenberger et al. "Targeted gene transfer to human hematopoietic progenitor cell lines through the c-kit receptor." *Blood* 87:472–478 (1996)
77. Crystal, R. G. 1997. Phase I study of direct administration of a replication deficient adenovirus vector containing *E. coli* cytosine deaminase gene to metastatic colon carcinoma of the liver in association with the oral administration of the pro-drug 5-fluorocytosine. *Human Gene Therapy* 8:985–1001.
78. Alvarez, R. D. and D. T. Curiel. 1997. A phase I study of recombinant adenovirus vector-mediated delivery of an anti-erbB-2 single chain (sFv) antibody gene from previously treated ovarian and extraovarian cancer patients. *Hum. Gene Ther.* 8:229–242.
79. Berzofsky, J. A. & Berkower, I. J. Immunogenicity and antigen structure. In: *Fundamental Immunology,* Third Edition. Chapter 8. Ed.:Paul, W. E. Lippincott-Raven, New York, N.Y., 1993.
80. Michieli, P., Li, W., Lorenzi, M. V., Miki, T., Zakut, R., Givol, D., and Pierce, J. H. *Oncogene* 12, 775–784, 1996.
81. Sambrook et al., *Molecular Cloning: A Laboratory Manual,* 2nd Ed., Cold Spring Harbor Laboratory, Cold Spring Harbor, N.Y., 1989.
82. U.S. Pat. No. 4,704,362.
83. Brake et al., 1984. Alpha-factor-directed synthesis and secretion of mature foreign proteins in *Saccharomyces cerevisiae*. *PNAS* 82:4642–4646.
84. *Remington's Pharmaceutical Sciences* (Martin, E. W., ed., latest edition), Mack Publishing Co., Easton, Pa.
85. Moss, B. 1991. Vaccinia virus: A tool for research and vaccine development. *Science* 252:1662–1667.
86. Di Fabio, S., et al. 1994. Quantitation of human influenza virus-specific cytotoxic T lymphocytes: Correlation of cytotoxicity and increased numbers of interferon gamma-producing CD8+ T cells. *Inter. Immunol.* 6:11–19.
87. Bukh, J., et al. 1994. Sequence analysis of the core gene of 14 hepatitis C virus genotypes. *Proc. Natl. Acad. Sci. U.S.A.* 91:8239–8243.
88. Gretch, D., et al. 1994. Assessment of hepatitis C virus RNA levels by quantitative competitive RNA polymerase chain reaction: High-titer viremia correlates with advanced stage of disease. *J. Infect. Dis.* 169:1219–1225.
89. Chayama, K., et al. 1997. Pretreatment virus load and multiple amino acid substitutions in the Interferon Sensitivity-Determining region predict the outcome of interferon treatment in patients with chronic genotype 1b hepatitis C virus infection. *Hepatology* 25:745–749.
90. *NIH Consensus Statement: Management of Hepatitis C.* Volume 15, Number 3, Mar. 24–26, 1997.
91. Kolykhalov, A. A., E. V. Agapov, K. J. Blight, K. Mihalik, S. M. Feinstone, and C. M. Rice. 1997. Transmission of hepatitis C by intrahepatic inoculation with transcribed RNA. *Science* 277:570–574.
92. Saito, T., G. J. Sherman, K. Kurokohchi, Z.-P. Guo, M. Donets, M.-Y. W. Yu, J. A. Berzofsky, T. Akatsuka, and S. M. Feinstone. 1997. Plasmid DNA-based immunization for hepatitis C virus structural proteins, immune responses in mice. *Gastroenterology* 112:1321–1330.
93. Hsu, H. H., M. Donets, H. B. Greenberg, and S. M. Feinstone. 1993. Characterization of hepatitis C virus structural proteins with a recombinant baculovirus expression system. *Hepatology* 17:763–771.
94. Belyakov, I. M., J. D. Ahlers, B. Y. Brandwein, P. Earl, B. L. Kelsall, B. Moss, W. Strober, and J. A. Berzofsky. 1998. The Importance of local mucosal HIV-specific CD8+ cytotoxic T lymphocytes for resistance to mucosal-viral transmission in mice and enhancement of resistance by local administration of IL-12. *J. Clin. Invest.* 102 (12):2072–2081.

TABLE 1

| Mouse | DNA Vaccine | Dose (μg) | Anti-CD8 | pfu/ovary |
|---|---|---|---|---|
| 1 | AC7 | 30 | – | $3 \times 10^3$ |
| 2 | AC7 | | | $4 \times 10^3$ |
| 3 | AC7 | | | $3 \times 10^3$ |
| 4 | AC7 | 30 | + | $2.5 \times 10^5$ |
| 5 | AC7 | | | $3.9 \times 10^8$ |
| 6 | AC7 | | | $1.5 \times 10^8$ |
| 7 | AC7-8A | 30 | – | <100 |
| 8 | AC7-8A | | | <100 |
| 9 | AC7-8A | | | <100 |
| 10 | AC7-8A | 30 | + | $1.8 \times 10^8$ |
| 11 | AC7-8A | | | $1.5 \times 10^8$ |
| 12 | AC7-8A | | | $1.3 \times 10^8$ |
| 13 | Mock | 100 | – | $2.4 \times 10^8$ |
| 14 | Mock | | | $2.8 \times 10^8$ |
| 15 | Mock | | | $1.6 \times 10^8$ |

What is claimed is:

1. An isolated peptide having the amino acid sequence of SEQ ID NO:1.

2. An isolated nucleic acid encoding the peptide of claim 1.

3. A vector comprising the nucleic acid of claim 2.

4. A method of producing an immune response in an immune cell of a subject, comprising contacting the cell with the peptide of claim 1.

5. A hepatitis C virus core polypeptide comprising an L→A substitution at amino acid position 139.

6. An isolated nucleic acid encoding the polypeptide of claim 5.

7. A vector comprising the nucleic acid of claim 6.

8. A method of producing an immune response in an immune cell of a subject, comprising contacting the cell with the polypeptide of claim 5.

9. A hepatitis C virus core polypeptide having the amino acid sequence of SEQ ID NO:2.

10. An isolated nucleic acid encoding the polypeptide of claim 9.

11. A vector comprising the nucleic acid of claim 10.

12. A method of producing an immune response in an immune cell of a subject, comprising contacting the cell with the polypeptide of claim 9.

13. A fragment of a hepatitis C virus core polypeptide having fewer amino acids than the entire hepatitis C virus core polypeptide, comprising the amino acid sequence of SEQ ID NO:1.

14. An isolated nucleic acid encoding the polypeptide fragment of claim 13.

15. A vector comprising the nucleic acid of claim 13.

16. A method of producing an immune response in an immune cell of a subject, comprising contacting the cell with the polypeptide fragment of claim 13.

* * * * *

UNITED STATES PATENT AND TRADEMARK OFFICE
CERTIFICATE OF CORRECTION

PATENT NO. : 6,685,944 B1
DATED : February 3, 2004
INVENTOR(S) : Jay A. Berzofsky et al.

It is certified that error appears in the above-identified patent and that said Letters Patent is hereby corrected as shown below:

Title page,
Item [75], Inventors, should read as follows:
-- Jay A. Berzofsky, Bethesda, MD (US); Stephen M. Feinstone, Washington, D.C. (US); Marian E. Major, Alexandria, VA (US); and Pablo Sarobe, Pamplona (ES). --

Signed and Sealed this

Third Day of May, 2005

JON W. DUDAS
*Director of the United States Patent and Trademark Office*